United States Patent
de Jong et al.

(10) Patent No.: US 11,284,632 B2
(45) Date of Patent: Mar. 29, 2022

(54) ECONOMICAL PROCESS FOR THE ISOLATION OF FUNCTIONAL PROTEIN FROM PLANTS

(71) Applicant: Nederlandse Organisatie voor toegepast-natuurwetenschappelijk onderzoek TNO, 's-Gravenhage (NL)

(72) Inventors: Govardus Adrianus Hubertus de Jong, 's-Gravenhage (NL); Peter Geerdink, 's-Gravenhage (NL); Paulus Josephus Theodorus Bussmann, 's-Gravenhage (NL); Nienke Hylkema, 's-Gravenhage (NL)

(73) Assignee: STICHTING WAGENINGEN RESEARCH, Wageningen (NL)

( * ) Notice: Subject to any disclaimer, the term of this patent is extended or adjusted under 35 U.S.C. 154(b) by 849 days.

(21) Appl. No.: 14/654,947

(22) PCT Filed: Dec. 20, 2013

(86) PCT No.: PCT/NL2013/050943
§ 371 (c)(1),
(2) Date: Jun. 23, 2015

(87) PCT Pub. No.: WO2014/104880
PCT Pub. Date: Jul. 3, 2014

(65) Prior Publication Data
US 2015/0335043 A1 Nov. 26, 2015

(30) Foreign Application Priority Data
Dec. 24, 2012 (EP) .................................. 12199355

(51) Int. Cl.
*A23J 1/00* (2006.01)
*C12N 9/88* (2006.01)
(Continued)

(52) U.S. Cl.
CPC ............... *A23J 1/006* (2013.01); *A23J 1/007* (2013.01); *A23J 3/14* (2013.01); *A23J 3/22* (2013.01);
(Continued)

(58) Field of Classification Search
CPC .................................. A23J 1/007; A23J 3/00
See application file for complete search history.

(56) References Cited

U.S. PATENT DOCUMENTS

| | | |
|---|---|---|
| 1,377,438 A | 5/1921 | Ricardo |
| 4,268,632 A | 5/1981 | Wildman et al. |

FOREIGN PATENT DOCUMENTS

| | | |
|---|---|---|
| WO | WO82/04066 | 11/1982 |
| WO | WO03028432 | 4/2003 |
| WO | 2011/078671 A1 | 6/2011 |

OTHER PUBLICATIONS

D'Alvise et al., "Removal of Polyphenols and Recovery of Proteins from Alfalfa White Protein Concentrate by Ultrafiltration and Adsorbent Resin Separations"—Separation Science and Technology, 35(15), 2000, pp. 2453-2472. (Year: 2000).*

(Continued)

*Primary Examiner* — Elizabeth Gwartney
(74) *Attorney, Agent, or Firm* — McDermott Will & Emery LLP

(57) ABSTRACT

The invention relates to a method for obtaining a protein from a plant material, wherein the method comprises the steps of i) mechanically disrupting the plant cells to obtain a plant juice in the presence of a reducing agent, ii) treating the plant juice to cause aggregation of chloroplast membranes, iii) removing the aggregated chloroplast membranes by precipitation and/or microfiltration, iv) subjecting the plant juice to ultrafiltration, and v) subjecting the soluble plant protein concentrate to hydrophobic column adsorption to remove residual chlorophyll, phenolic compounds and (Continued)

off-odors in a single column passage. The present invention also pertains to an apparatus and system for plant protein isolation based on this method. The isolated proteins can be economically obtained in batch scale and in large scale. Further, the invention is directed to a protein obtained by the method of the invention, a food product comprising thereof, and a use thereof.

33 Claims, 8 Drawing Sheets

(51) Int. Cl.

| | |
|---|---|
| A23J 3/22 | (2006.01) |
| A23J 3/14 | (2006.01) |
| B01D 11/00 | (2006.01) |
| B01D 61/14 | (2006.01) |
| B01D 15/08 | (2006.01) |
| A23P 30/40 | (2016.01) |
| A23L 33/105 | (2016.01) |
| A23L 33/185 | (2016.01) |
| A23L 29/10 | (2016.01) |

(52) U.S. Cl.
CPC ............ *A23L 29/10* (2016.08); *A23L 33/105* (2016.08); *A23L 33/185* (2016.08); *A23P 30/40* (2016.08); *B01D 11/00* (2013.01); *B01D 15/08* (2013.01); *B01D 61/145* (2013.01); *B01D 61/147* (2013.01); *C12N 9/88* (2013.01); *A23V 2002/00* (2013.01); *C12Y 401/01039* (2013.01)

(56) References Cited

OTHER PUBLICATIONS

Fiorentini et al., "The proteins from leaves", Qual Plant Plant Foods Hum Nutri, 32, (1983), pp. 335-350. (Year: 1983).*
Betschart et al., "Extractability and Solubility of Leaf Protein", J. Agr. Food Chem., vol. 21, No. 1, 1973, pp. 60-65. (Year: 1973).*
International Search Report dated Apr. 14, 2014 from corresponding PCT Application No. PCT/NL2013/050943.
Barbeau et al., "Formation of a Gel from a Heated Emulsion of Alfalfa Leaf Protein and Peanut Oil," Journal of Food Science, vol. 52, 3 pages (1987).
Barbeau et al., "Ribulose Bisphosphate Carboxylase/Oxygenase (Rubisco) from Green Leaves-Potential as a Food Protein," Food Reviews International, 4:93-127 (1988).
Danielsson et al., "Quantification of Photosystem I and II in Different Parts of the Thylakoid Membrane from Spinach," Biochimica et Biophysics Acta, 1608:53-61 (2004).
Douillard et al., "Leaf Protein for Food Use: Potential of Ruisco," New and Developing Sources of Food Proteins, pp. 307-342 (1394).
Eakin et al., "Alfalfa Protein Fractionation by Ultrafiltration," Journal of Food Science. 43:544-552 (1976).
Hincha, "Effects of Calcium-Induced Aggregation on the Physical Stability of Liposomes Containing Plant Glycolipids," Biochimica et Biophysics Acta, 1611:180-186 (2003).
Jervis et al., "Purification Technologies for Plant Protein," Journal of Biotechnology, 11:161-198 (1989).
Knuckles et al., "Soluble Protein from Alfalfa Juice by Membrane Filtration," Journal of Agricultural and Food Chemistry, 23:209-212 (1975).
Knuckles et al., "Functional Properties of Edible Protein Concentrates from Alfalfa," Journal of Agricultural and Food Chemistry, 30:748-752 (1982).
Pierpoint,"The Extraction of Enzymes from Plant Tissues Rich in phenolic Compounds," Methods in Molecular Biology. 244:65-74 (2004).
Rohm and Haas Company, "Amberlite XAD16", pp. 1-4 (2003).
Weisz et al: "Sustainable sunflower processing-I. Development of a process for the adsorptive decolorization of sunflower [*Helianthus annuus* L.] protein extracts," Innovative Food Science and Emerging Technologies, 2010, 11, 733-741.
Pickardt et al: "Processing of low polyphenol protein isolates from residues of sunflower seed oil production," Procedia Food Science, 2011, 1, 1417-1424.
Tilay et al: "Preparation of ferulic acid from agricultural wastes: Its improved extraction and purification," J. Agric. Food Chem., 2008, 56, 7644-7648.
D'alvise et al: "Removal of polyphenols and recovery of proteins from alfalfa white protein concentrate by ultrafiltration and absorbent resin separations," Separation Science and Technology, 2000, 35:15, 2453-2472.
Loomis et al: "Adsorbent polystyrene as an aid in plant enzyme isolation", Phytochemistry, 1979, 18, 1049-1054.

* cited by examiner

ECONOMICAL PROCESS FOR THE ISOLATION OF FUNCTIONAL PROTEIN FROM PLANTS

RELATED APPLICATIONS

This application is the U.S. National Stage of International Application No. PCT/NL2013/050943, filed Dec. 20, 2013, published in English, and claims the benefit of European Application Number 12199355.4, filed on Dec. 24, 2012, the entire teachings of the above applications are incorporated herein by reference.

FIELD OF THE INVENTION

The present invention is in the field of agriculture, and in particular the field of protein extraction from crop plants. The invention is directed to a method for obtaining a protein, in particular a functional protein, from a plant material. The invention is further directed to a functional protein obtained by the method of the invention, a food product comprising thereof, and a use thereof. The invention is further directed to a preferably mobile extraction system for extracting functional protein from a plant material.

BACKGROUND OF THE INVENTION

Proteins obtained from plant materials, are interesting as an ingredient for the food industries. Highly purified plant proteins have a fantastic nutritional value. For example, Rubisco is also readily digestible, non-allergic, and excellent in foaming, gelation, and solubility. These proteins with high nutritional values are in particular important. These proteins can add nutrients to food, and improve the quality and the mouthfeel of food, or act as meat substituents or substituents in diet meals. These plant proteins are tremendously valuable. Also, plant proteins can provide sufficient essential nutrients to the growing population in the world, which cannot be provided by animal proteins. Hence, it is desired to develop a method for obtaining a protein, in particular a food-grade protein from plant materials.

However, plant materials contain not only various proteins, but also contains undesired compounds and organelles which may interfere with the isolation of proteins from the plant materials. Moreover, some compounds existing in the plant materials may bring undesired qualities, such as color, smell, or taste, to the protein.

The most important classes of compounds challenging the purification of plant proteins are: (i) polyphenols; (ii) pigments such as chlorophyll and carotenoids; (iii) oxidized lipids, and; (iv) proteases. Not all impurities interfere with the commercial applications of proteins. However, the pigments which are abundantly present in plants seriously limit the applications. The problem is that polyphenols react with amino acids, which change the nutritional value of proteins, and may cause digestive problems. Moreover, during or after the purification of a plant protein, protein-bound oxidized phospholipids may produce off-odors or off-flavors or may give themselves rise to off-odor or off-flavor-causing compounds. In general, a smell of freshly cut green grass is associated with volatile compounds generated though oxidation of plant oils by lipoxygenases. For soy and leaf proteins, enzymatic oxidation by lipoxygenases and polyphenoloxidases (PPO) plays an important role in the synthesis of off-odor or off-flavor compounds and reactive oxidation products of polyphenols, both of which are notoriously hard-to-remove compounds. Moreover, endoproteases in leaves hinder purification of proteins by cutting target proteins, which again causes off-odors or off-flavors but also reduces the functionality of the target proteins. The presence of pigments, polyphenols and/or off-odors or off-flavors seriously hampers the use of plant-derived proteins as a nutritional or functional protein ingredient in foods.

In order to obtain a protein without any undesired qualities and/or compounds, several methods for obtaining a protein have been studied and developed. However, a suitable method for obtaining plant proteins that retain their techno-functional properties (e.g. for gelation, emulgation, stabilization, water absorption, binding, dispersion, netting, improvement of structure, mouthfeel, fat emulsification and foaming) after isolation on an industrial scale was hitherto not found, because removal of every adverse contaminant proved simply too expensive.

In order to extract a protein from a plant material, the plant material is usually treated with several chemicals, such as strong acids and/or strong alkalis, and is further processed under extreme temperatures, pressures, and external forces. A large amount of chemicals and an equally large amount of equipment is required to obtain a plant protein. This is of great influence on the economics of harvesting extract plant proteins on an industrial scale. Moreover, since chemicals, extreme temperatures, pressures, and external forces are required during the process, the functionality of plant proteins is damaged or even lost.

Some methods for obtaining a plant protein have advocated the use of anti-oxidants during the process. However, such processes usually require large amounts of anti-oxidants which inevitably results in high costs. Furthermore, the plant proteins obtained still contain a large amount of phenolic compounds, which are undesirable for several reasons.

Phenolic compounds, or polyphenols, are found in large amounts in plant material, in particular in plant leaves. Polyphenols play an important role. For instance, polyphenol is an antioxidant, and a high level of polyphenol can sometimes act as natural preservative against rot. Some plant polyphenols are antimicrobial substances, such as phytoalexins. However, presence of polyphenols in a food-grade protein is not desirable. Polyphenols are anti-nutrients because polyphenols can interfere with the absorption of nutrients. Moreover, during the process of isolating proteins from plant materials, polyphenols often bind covalently to the proteins, which binding is irreversible. Hence, there is a need to have a separation technique to isolate proteins, preferably food-grade proteins, with low content or without polyphenols in the final product.

WO82/04066 and U.S. Pat. No. 4,268,632 discloses a process for isolating proteins from plant leaves, in particular tobacco leaves. After the leaves are ground into a pulp, the supernatant part of the pulp is stored under a temperature at or below room temperature to obtain a Rubisco in crystalline form. However, such processes are in particular designed for isolating Rubisco only from tobacco leaves, rather than from other kinds of plant materials. Rubisco from tobacco behaves differently from Rubisco of other plant sources. Rubisco from tobacco is amenable to crystallization, while Rubisco from other plants is generally not. As a consequence, different separation and/or purification techniques must be used. For this reason, the processes as described in WO82/04066 and U.S. Pat. No. 4,268,632, are based on crystallization of Rubisco, are not generally applicable.

Enzymatic proteins, such as Rubisco, are easily damaged. Heat treatment denatures the protein and destroys the functionality thereof. For example, denaturing of Rubisco leads to exposure of a hydrophobic moiety, and hence decreases the solubility of Rubisco and increases the binding of polyphenols thereto. In general, the purification of a protein should be as mild as possible in order to retain the functionality. Moreover, use of a large amount of chemicals and/or experimental facilities to monitor temperature results in higher costs. Hence, use of denaturing agents, high temperature, and strong acids or alkalis should be avoided.

Another problem of isolating a protein from plant materials is loss of significant amount of proteins. For example, the association of Rubisco with the thylakoid membranes often results in the loss of the majority of Rubisco during the process. This association is influenced by different kinds of salts, concentration of salts, and pH value of extraction buffer. For instance, in the chloroplast of spinach leaves, hypotonic disruption results in that the association of Rubisco with thylakoid membranes increases in proportion to the concentration of $MgCl_2$ or the ionic strength. Moreover, the association of Rubisco with the thylakoid membranes was found to be maximal at pH 8. As Rubisco is negatively charged at pH 8, the association with the negatively charged layer in the thylakoid membranes surface is probably bridged by $Mg^{2+}$. The attachment of Rubisco to thylakoid membranes can be broken up by shaking in a Vortex mixer. Also, Rubisco can be liberated from the thylakoid membranes by the treatment with EDTA.

Therefore, it is very problematic to isolate proteins from plant materials. However, as mentioned above, plant proteins have many beneficial applications, especially when compared to animal proteins. There is a need to develop a method for obtaining plant proteins in a economical and efficient way.

In agricultural industries, sugar beets (*Beta vulgaris*) are grown on a very large scale. The beets are generally used to produce sugar, while the leaves and stems of the beets are plowed under the ground or used as silage. The added value of the leaves and stems is presently very small. The present invention aims to upgrade the value of such leaves.

SUMMARY OF THE INVENTION

The present invention now provides a method for obtaining a protein from plant materials on an industrial scale. The present invention is based on removal of chloroplast membranes, chlorophyll, polyphenols, and/or undesired compounds from the juicy of plant materials. The inventors surprisingly discovered that the method of the present invention can be carried out with low cost, and that the proteins obtained by the method have high marketable value and are food-grade.

Furthermore, the inventors discovered that the proteins obtained by the method of the invention are free of polyphenols, off-flavors, and unpleasant colors, and hence have better qualities and wider applicability. The separation technique of the present invention is aimed at keeping the proteins in a solution until the proteins are dried. Furthermore, the present invention provides an economical method. In addition, polyphenols separated from the target proteins can be further eluted, purified, and used in industrial applications.

Up to now, plant-purified proteins could not be produced free of polyphenols. The present invention advantageously provides a method for obtaining a plant protein, which is cheap, efficient, and can be used on large scale. Moreover, the present inventors surprisingly discovered that the separation of off-flavors, chlorophyll, and phenolic compounds is in a single step by using hydrophobic adsorption. The advantage is that a high capacity purification process is attained that for the first time can be performed on an industrial scale.

In one aspect, the present invention provides a method for isolating a soluble plant protein from a plant material on an industrial scale, wherein the method comprises the steps of:

i) mechanically disrupting the plant cells of said plant material to obtain a plant juice, wherein before, during, or after the step of disrupting the plant cells an extraction composition comprising at least one of a reducing agent and a divalent ion source is added to said plant material, said plant cells and/or said plant juice, ii) treating the plant juice to cause aggregation of chloroplast membranes, iii) separating said aggregated chloroplast membranes from the soluble plant protein in said treated plant juice by precipitation and/or microfiltration to provide a plant juice supernatant or plant juice permeate comprising the soluble plant protein, iv) subjecting the plant juice supernatant or plant juice permeate to ultrafiltration, optionally in diafiltration mode, to provide a soluble plant protein concentrate, preferably comprising 25-50 wt % of protein, wherein said soluble plant protein concentrate is essentially free of salts and phenolic compounds, and v) subjecting the soluble plant protein concentrate to hydrophobic column adsorption to thereby separate in a single column passage the residual chlorophyll, phenolic compounds and off-odors from the soluble plant proteins to provide a column permeate comprising isolated soluble plant protein that is essentially free of chlorophyll and off-odors (in addition to being essentially free of salts and phenolic compounds as a result of step iv).

The step i) of mechanical disruption of the plant cells of the plant material may occur by mechanically homogenization of the plant material. The use of a screw pressing homogenizer is very suitable and a preferred embodiment in aspects of this invention.

In a preferred embodiment of a method of the present invention the extraction composition comprises at least one of a reducing agent and a divalent ion and preferably further comprises at water and/or a buffering agent. The divalent ion is preferably present in an amount that—when mixed with the juice—causes or at least enhances precipitation of chloroplast membranes therein. Preferably, the chelating agent, buffering agent and/or divalent ion source are food grade.

In another preferred embodiment of a method of the present invention the reducing agent is metabisulfite.

In yet another preferred embodiment the plant juice after addition of said extraction composition comprises a dry matter content of up to 10 wt % based on the total weight of the plant juice.

A method for isolating a soluble plant protein from a plant material may comprise a heating step for precipitation of chlorophyll-containing membranes. Preferably, the heating of the plant juice involves heating to a temperature of between about 40° C. to 60° C. This constitutes a step of mild-heat treatment. Preferably said mild-heat treatment comprises exposing the juice to a temperature of between about 40° C. to 60° C. Preferably the temperature of the mild-heat treatment is in the range of 40-55° C., preferably in the range of 40-50° C., and even preferably 40-45° C.

Preferably the mild-heat treatment is only short, such as between 1 minute and 3 hours, preferably between 1 minute and 1 hour, more preferably between 5 and 50 minutes, more preferably between 10 and 30 minutes, more preferably about 15-25 minutes, suitably 20 minutes. Mild-heat treatment is the preferred step for chloroplast membrane removal.

The mild-heat treatment is not beneficial for the functionality of the protein. Therefore, the mild-heat treatment is only short, and is preferably followed by a rapid cooling of the heated juice (for instance within 1 minute to 1 hours, more preferably within 1-30 minutes, more preferably within 1-10 minutes, the temperature of the heat treated juice is back to ambient levels, or if needed, even further reduced to cooler temperatures. Hence, after the mild heat treatment or heating step, the heated juice is preferably cooled, preferably by forced cooling. Preferably the heated juice is cooled in less than 60 minutes, preferably less than 30 minutes, more preferably less than 10 min, 9 min, 8 min, 7 min, 6 min, 5 min, 4 min, 3 min, 2 min, or 1 minute to a temperature from about 50° C. to a temperature of about 15° C., more preferably to a temperature of about 10° C., 9° C., 8° C., 7° C., 6° C., 5° C., 4° C., 3° C., 2° C., or 1° C. in that time frame.

Alternatively to the mild heat treatment, or in addition to it, the juice may be treated by a divalent ion to induce aggregation (flocculation) of the chlorophyll membranes. Divalent ion treatment is most effective under a low (0.1-0.5% ww) metabisulfite regimen, optionally 0% w/w metabisulfite.

The step of treating the plant juice to cause aggregation of chloroplast membranes, thus may involve heating to cause aggregation, or may involve allowing the chloroplast membranes to aggregate in the presence of a divalent ion such as a calcium salt, for instance in a flocculation tank.

In another preferred embodiment of a method of the present invention said precipitation step involves centrifugation of the heated and optionally cooled and/or divalent ion treated juice to provide a pellet of aggregated chloroplast membranes and a plant juice supernatant comprising the soluble plant protein. The precipitation step is aimed to precipitate solids from the plant juice which have developed as a result of heat-induced aggregation. Such precipitation may be added by the use of centrifuges or hydro-cyclones. Alternatively, the aggregates may be allowed to sink-out under normal gravity, but this may be time consuming. It has now been found that the addition before the heating step and/or instead of the heating step to the plant juice of a divalent ion in an amount that causes flocculation of the chloroplast membranes thereby enhancing precipitation of chloroplast membranes, will result in efficient removal of the chloroplast membranes. This allows for the very efficient removal of the green chlorophyll color from the proteins of interest. A suitable amount of the divalent ion is about 0.00001 to 1 M, more preferably 10-500 mM, still more preferably 50-300 mM. Thus a method of the invention wherein the extraction composition comprises a divalent ion preferably involves a process wherein step iii) comprises separating the aggregated chloroplast membranes from the soluble plant protein in the plant juice by divalent ion-induced precipitation. Suitable divalent ions for use in aggregation by flocculation of the thylakoid membranes include calcium (Ca), magnesium (Mg), beryllium (Be), zinc (Zn), cadmium (Cd), copper (Cu), iron (Fe), cobalt (Co), nickel (Ni), tin (Sn), strontium (Sr), barium (Ba), and radium (Ra), preferably the soluble salts thereof. A divalent ion according to the invention is preferably any food-grade divalent ion suited for addition to a protein extract. By a divalent ion is meant an ion with 2 valences. The divalent ions may be either cations (positively charged) or anions (negatively charged). Divalent cations are preferred. Preferred divalent ions of the invention are ions of calcium, zinc, magnesium, and iron, and combinations thereof, especially calcium (II), magnesium (II), zinc (II), and iron (II), and in particular the soluble divalent salts of these elements. CaCl2 is highly preferred, as are Ca(NO3)2, and FeCO3.

Alternatively to precipitation, or, preferably, in addition to it, the method may involve the step of microfiltration. Said microfiltration comprises filtering the heated and preferably cooled juice through a filter having a pore size in the range of 0.1-0.5 µm. The pore size of the microfilter is preferably such that it retains membranes, chlorophyll, tannin, virus, bacteria and/or aggregates thereof from said juice while allowing passage of soluble proteins. If microfiltration is used, the step of microfiltration preferably comprises the use of a filter having a pore size in the range of 0.2-0.5 µm. The step of microfiltration is beneficial, and can be performed in addition to the mild-heat treatment step because also other undesirable components of the juice can be removed by this step. The microfiltration preferably removes residual (chloroplast or cell) membranes, chlorophyll, tannins, virus, and/or bacteria from the juice. The step of microfiltration may be performed by use of a filter having a pore size in the range of 0.2-0.45 µm, more preferably in the range of 0.22-0.45 µm, more preferably in the range of 0.22-0.4 Ξm, even more preferably in the range of 0.2-0.35 µm, and still more preferably in the range of 0.2-0.3 µm. Preferably the step of microfiltration is used to prevent clogging of the subsequent ultrafilter.

The present invention further preferably comprises the step of ultrafiltration of the plant juice in order to concentrate the proteins therein and remove the bulk of the polyphenols. When using ultrafiltration, this preferably comprises the use of a filter in the range of 20-100 kDa. Preferably the ultrafilter has a molecular size cut-off in the range of about 20-90 kDa, more preferably in the range of about 20-80 kDa, more preferably in the range of about 20-70 kDa, still more preferably in the range of about 20-60 kDa, and even more preferably in the range of about 20-50 kDa, 20-40 kDa, 25-35 kDa, and most preferably in the range of about 27-33 kDa. When using diafiltration, this preferably comprises the removal of salts.

Preferably the ultrafiltration step concentrates the protein in the juice such that the juice comprises about 25-50% wt % dry matter based on the total weight of the juice. Preferably the wt % of the dry matter based on the total weight of the juice before column filtration and drying is about 25-45 wt %, preferably about 25-40 wt %, preferably about 25-35 wt %, and even preferably about 27-33 wt % based on the total weight of the juice. This low amount of water facilitates reduced transport volumes between the location of protein concentrate production on the one hand and purification and drying on the other.

In another preferred embodiment of a method of the present invention the method comprises the step of hydrophobic column adsorption. Such column absorption comprises the use of a column packed with a hydrophobic adsorptive resin. A very suitable resin for removal of the residual phenolic compounds, off-odor or off-flavors, and residual chlorophyll was found to be a non-ionic crosslinked aromatic or aliphatic polymer resin, preferably a non-ionic crosslinked polystyrene resin, even more preferably a macroreticular styrene-divinylbenzene copolymer matrix. Such resins are commercially available under the names of Amberlite™ XAD-2, Amberlite™ XAD-4 and Amberlite™ XAD-16, Amberlite™ XAD 16N, Amberlite™ XAD 1180N, and Amberlite™ XAD 1600N (Sigma, St Louis, USA). The highly porous aliphatic acrylic adsorbent resin Amberlite™ XAD 7HP or highly porous phenolic adsorbent resin Amberlite™ XAD 761 (both available form Sigma, St Louis, USA) are also suitable for removal of the phenolic compounds. Comparable resins from other suppliers are equally suitable. Amberlite™ XAD-16 is highly preferred as it results in excellent and almost simultaneous (or single pass) removal of residual chlorophyll, phenolic compounds, and off-odor or off-flavor-causing compounds from the juice.

Other suitable and exemplary materials with the function of hydrophobic adsorption are talc, hydrophobized calcium carbonate, hydrophobized bentonite, hydrophobized kaolinite, hydrophobized glass, or a mixture thereof. Many hydrophobic adsorptive materials are commercially available, such as Toyopearl® Butyl-650, Tenax® TA™, Phenyl Sepharose™, Butyl Sepharose™, SOURCE™ 15 ethyl and SOURCE™ 15 phenyl media and Carbograph 1TD™. Preferably, the hydrophobic adsorption is performed by a column packed with hydrophobic adsorptive material, such as in the form of a matrix or beads. Still preferably, the hydrophobic adsorption is performed by using an non-ionic crosslinked polystyrene resin, most preferably Amberlite™ XAD 16 resin. The relative reduction in the polyphenol-concentration during the purification process as following the step of hydrophobic adsorption, as may for instance be determined by measuring and comparing the absorption spectrum of the juice at 280 nm before and after the step of hydrophobic adsorption, is preferably at least 80 wt % of the concentration in the raw juice just after pressing. Preferably, the relative reduction is at least 90 wt %, more preferably at least 95 or 98 wt %.

In another preferred embodiment of a method of the present invention the method further comprises a step vi) of drying the column permeate from the hydrophobic adsorption column, which permeate comprises soluble plant protein. Upon drying, which is preferably performed by lyophilisation or spray drying, a powder of functional plant protein is provided that is essentially odourless, and essentially free of chlorophyll and polyphenols. When using such drying methods, the dry matter content can be higher than 50 wt %, such as 60 wt %, 70 wt %, 80 wt %, 85 wt %, 90 wt %, 95 wt %, or ever higher, based on the total weight of the composition.

In order to prevent deterioration of the proteins during the isolation process, it is preferred that steps i), iv), and v), and preferably also vi) according to a method of the present invention as described above are performed under low temperature. A low temperature is preferably a temperature in the range of about 0-15° C., more preferably in the range of about 1-10° C., and even more preferably the temperature in the range about 2-5° C.

Also in order to prevent deterioration of the proteins during the isolation process, it is preferred that the processing time to complete process steps i)-v), and preferably also step vi), is no more than 1 day (i.e. within 16-24 hrs), more preferably within 8 hours. Because protein deterioration starts immediately following the harvest of the plant material, it is preferred that the processing time from harvest of the plant material to completion of process steps v), and preferably also vi), is no more than 1 day, preferably less than 8 hours. In a highly preferred embodiment of a method of this invention the completion of the ultrafiltration step (iv) for removal of polyphenols is completed within 2 hrs following the production of the juice from raw plant material. This rapid process is ultimately beneficial for improving the yield of the process and results in a material having less impurities.

In order to arrive full circle and start another round of protein isolation using the same equipment, it is preferred that the method further comprises the step of regenerating the hydrophobic adsorption column. Such regeneration is preferably accomplished by the use of ethanol as a desorption eluent to elute column-adsorbed compounds from the column.

As a plant material, any type of plant, preferably a leaf thereof, from which a plant juice can be pressed is suitable for use in the present method. Very suitable plant materials are harvest waste materials. The plant material may preferably be selected from the group consisting of duckweed, algae, grass, leaves of potato and beets, including leaves of beetroot, spinach beet, chard, sugar beet, sea beet, and Mangel beet.

Although in principle any soluble protein may be isolated from a plant material using the above-described method, it is preferred that the soluble protein is ribulose 1,5-diphosphate carboxylase oxygenase (Rubisco).

It is foreseen that the method of the present invention is performed as an in-field process, whereby the harvest waste materials are processed in parallel to the harvesting of the agriculturally beneficial crops, it is preferred that as many process steps as possible are performed on-site during harvest. Hence, method steps i)-iv) (pressing to ultrafiltration) are preferably performed on a first location (e.g. a field location) using a plant (waste) material harvesting apparatus, and wherein method steps v) and vi) (column filtration and drying) are performed at a second, separate location. The said plant waste material harvesting apparatus is preferably mobile, whereas the steps of column filtration and drying are preferably performed at a separate, preferably static, location.

In another aspect, the present invention pertains to a protein isolate obtained by a method according to the invention as described above. Such a protein isolate is distinguishable from other plant protein isolates in that, in addition to being odourless and essentially free of chlorophyll, it preferably comprises low amounts of tannin (a polyphenol). Preferably the content of tannin in the final protein product is low due to a reduction in the tannin content of the juice after hydrophobic adsorption of at least 50 wt %, preferably 75 wt %, more preferably 90 wt %. Preferably the content of tannin is in the range of 0.05-1.0 wt % based on the total weight of the juice. Still more preferably the content of the tannin is in the range of 0.05-0.1 wt %. The low tannin content of the protein of the invention is due to a very effective polyphenol-removal step. Preferably the content of polyphenols in the final protein product is low due to a reduction in the polyphenol content of the juice after hydrophobic adsorption of at least 50 wt %, preferably 75 wt %, more preferably 95 wt %.

In yet another preferred embodiment of a method of the invention, the protein is a functional protein, meaning that it has retained its biological activity (expressed for instance as enzymatic activity per milligram of total protein, e.g. in $\mu mol \cdot min^{-1} \cdot mg^{-1}$) or structure (expressed for instance as functionality or solubility) for at least 50%, 60%, 70%, 80%, 90%, or higher compared to the native activity or structure of the protein.

In another aspect, the present invention provides a food product comprising a protein isolate of the present invention.

In yet another aspect, the present invention provides the use of the protein isolate of the present invention as a thickening agent, a foaming agent, an emulsifier, a gelling agent and/or a texturizing agent. Besides the possibilities regarding the functional properties of the plant protein, the nutritional value of the protein proves to be high in essential amino acids, making the protein an interesting replacement for meat and soy protein and other legume proteins.

In yet another aspect, the present invention provides an apparatus for isolating a soluble plant protein from a harvested plant material, said apparatus comprising:

i) a screw press for pressing a raw plant juice from a harvested plant material, said press having a harvested plant material inlet and a raw juice outlet;

ii) a receptacle for holding an extraction composition which composition comprises at least one of a reducing agent and a divalent ion, said receptacle having an outlet in fluid communication with the harvested plant material before entering the screw press, the plant material or plant juice during pressing in the screw press, or the raw juice obtained, iii) a combination of a heating unit for heating the plant juice and a a cooling unit for cooling of the heated plant juice, and/or a flocculation tank for allowing divalent ion-induced flocculation of the chlorophyll membranes in the plant juice;

iv) a precipitation unit (such as a continuous centrifuge or hydrocyclone) and/or microfiltration unit for separating heat-aggregated solids from heated plant juice comprising the soluble plant protein, v) an ultrafiltration unit for separating soluble plant protein from soluble polyphenols having a retentate outlet;

vi) a pump for driving the raw plant juice from the screw press through, subsequently, the heating unit, the cooling unit, the precipitation and/or microfiltration unit and the ultrafiltration unit to provide at the ultrafiltration unit retentate outlet a soluble plant protein concentrate, wherein said soluble plant protein concentrate is essentially free of salts and phenolic compounds, and wherein the plant protein concentrate comprises an increased concentration of soluble plant protein, preferably at a concentration of 25-50 wt % of protein;

vii) a single pass hydrophobic adsorption column comprising a hydrophobic adsorptive resin, preferably a non-ionic crosslinked polystyrene resin, said column having a further having a permeate outlet;

viii) a drying unit for drying said column permeate.

In a preferred embodiment of an apparatus of the invention for isolating a soluble plant protein the apparatus comprises a first, preferably mobile, part comprising units i)-vi) and a second separate, preferably immobile, part comprising units vii) and viii).

The skilled person will understand that the first and second part of the apparatus together provide a system for isolating a soluble plant protein, wherein the system may further comprise the use of transport means between the various process units. One suitable configuration of the system and apparatus of the invention is provided in the attached drawings.

DETAILED DESCRIPTION OF THE INVENTION

Definitions

Figure 1:
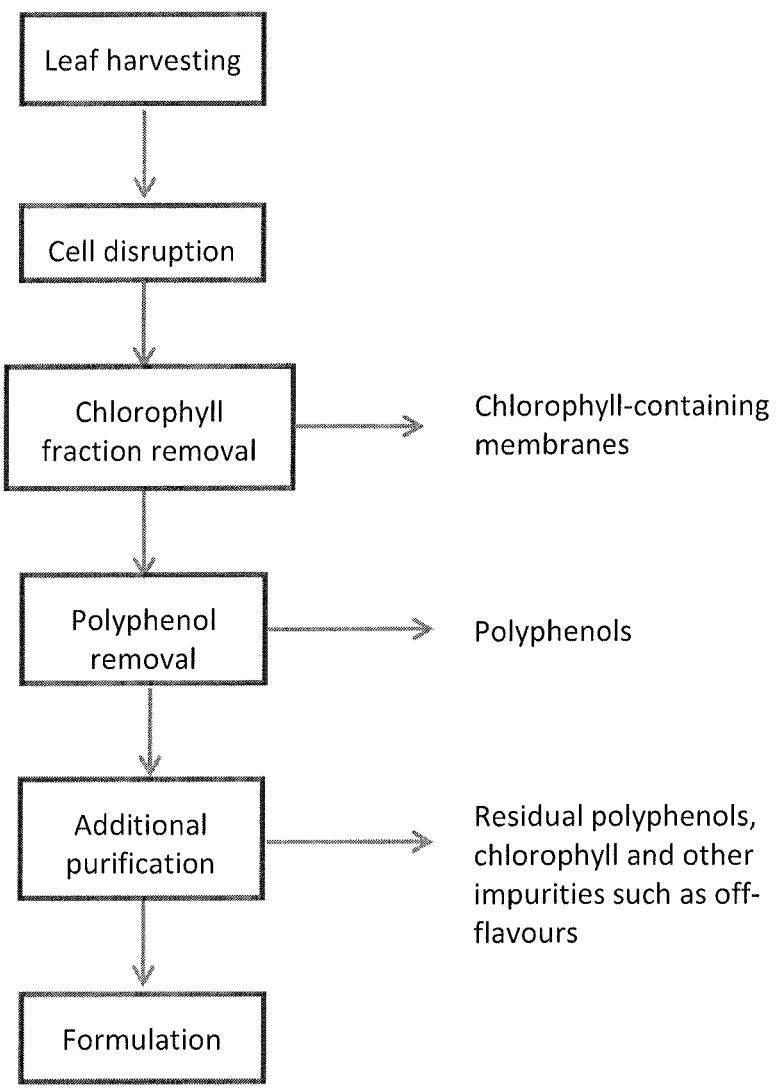
FIG. 1 shows a process scheme of the method for obtaining a protein from a plant material in batch scale.
Figure 2:
FIG. 2 shows the final product obtained by the method of the present invention as described herein. The dried protein powder is white, essentially without polyphenols, and was odourless.

As used herein, the terms "optional" and "optionally" refer to that the subsequently described event or circumstance may or may not occur, and that the description includes instances where said event or circumstance occurs and instances where it does not.

It will be understood that the terms "preferably", "more preferably", "even more preferably" and "preferred" as used throughout the specification refer to one or more favoured exemplary embodiments of the invention and therefore is not to be interpreted in any limiting sense.

As used herein, the term "obtained" refers to that proteins are extracted or isolated from plant materials. The proteins can remain in a solution or can be dried or further purified. The proteins subjected to a method of the invention are originally inside the cells of the plant material. By the method of the invention, the cells of the plant materials are disrupted and hence proteins in the cells are released or liberated from the cell structures and cell substructures, and separated from non-protein components, meaning that they are extracted and can be isolated.

The term "isolated" as used herein with respect to a protein refers to a protein (e.g., a polypeptide or enzyme) that is relatively free of other compounds or molecules such as nucleic acids, lipids, sugars or other molecules it normally is associated with in a cell. In general, an isolated protein constitutes at least about 25%, more preferably about 50% still more preferably about 75% by weight of a sample containing it, more preferably about 90% of a sample containing it, more preferably about 95% of the sample containing it, or more preferably about 99% of a sample containing it.

The term "purified" as used in reference to proteins denotes that the protein is present in the substantial absence of other biological macromolecules, e.g., polynucleotides, carbohydrates, and the like. The term "purified" as used herein preferably means at least 95% by weight, more preferably at least 99.8% by weight, of protein present (but water, buffers, and other small molecules, especially molecules having a molecular weight of less than 1000 daltons can be present).

As used herein, the term "plant material" refers to that any portion of a plant. Plant material can be any one selected from stem, root, fruit, leaves, and seeds. Further, the plant material can be obtained from various species of plants. For instance, from duckweed, algae, beetroot, spinach beet, chard, sugar beet, sea beet, Mangel beet, or a plant of the species of *Beta vulgaris*. The plant material is preferably not a tobacco leaf.

As used herein, the terms "disrupting" and "disruption" refer to that the cells of the plant materials are broken by external and/or internal forces to the effect that the cell content is liberated therefrom.

As used herein, the term "juice" refers to that a liquid originating from disrupted plant material, which liquid may optionally comprise a buffer such as an extraction buffer. The juice may take the form a pulp, a slurry, or a suspension. The juice comprises soluble and insoluble parts of a plant material. Suitably, the juice is obtained by pressing, mashing, squeezing, or homogenizing a plant material.

As used herein, the term "functional" refers to a protein having native functionality or activity, preferably both in a solution and in a dried form. A protein loses its functionality or activity upon denaturing, such as after exposure to extreme temperature, pressure, or denaturing or hydrolysing chemicals, which results in a structural change of the macromolecule (i.e. denaturation). Usually the structure of the protein irreversibly changes so that the protein cannot perform the original functionality or activity. Preferably, the functionality of a protein is enzymatic functionality.

As used herein, the term "food-grade" refers to a protein or a compound which is edible for animals, in particular mammals. The protein or the compound is not harmful, non-toxic and/or not anti-nutritional. Suitably, the protein or the compound can increase the quality, nutrition, mouthfeel, texture, and/or marketable value to a food product.

As used herein, the terms "off-flavor" and "off-odor" are used interchangeably herein and refer to a compound, a component, or a substance which can produce or create an unpleasant taste and/or smell, such as a light activated compound, a sunlight activated compound, a sun struck compound, a rancid compound, a butyric compound, a goaty compound, a bitter compound, a cardboardy compound, a papery compound, a metallic compound, a tallowy compound, a oily compound, a painty compound, a fishy compound, an old compound, a cooked compound, a scorched compound, a caramelized compound, a musty compound, an oxidized compound, or combinations thereof. Off-odors are not desirable in a food-grade product. Usually, off-odors are caused by deterioration and/or contamination of a protein, a compound, or a material. Examples of off-odor-causing compounds include small molecular weight phytochemicals; diacetyl; alpha-terpeneol; carvone; degraded products of d-limonene; oxidized products of d-limonene; 2,4,6 trichloroanisole; terpene-4-ol; lipids containing a fatty acid moiety such as free fatty acids; phospholipids including lysophospholipids, and other phospholipids; glycerides including triglycerides, diglycerides, and monoglycerides; and cholesterol esters, and; the hydrolyzed by-products of these lipids. The fatty acid moieties in these lipids, such as polyunsaturated fatty acid moieties, oxidize to contribute to off-odors. One of the most important off-odors is a grassy smell.

As used herein, the term "grassy smell" refers to a compound, a substance, or a component which carries a smell essentially perceived as that of (freshly cut) grass. Whether a product according to the invention is essentially free of the off-odors can best be determined by using a trained panel. An trained panel of human subjects can be used to evaluate the odor intensity of the protein isolate (preferably in concentrated liquid form or in dried form). Refrigerated samples may be tempered about at room temperature (22° C.) before presenting to the sensory panels. Samples of 1 or more grams (e.g. 3 g) can be presented in a capped vial (20 ml), and a scale of 0-5 may be used to rate the samples for off-odor intensity (very weak=0 and very strong=5). The protein isolate obtained by methods of this invention provide (on average) off-odor intensitie below level 3, preferably below level 2, most preferable below level 1.

As used herein, the term "residual" or "remaining" refers to the chlorophyll remained in the juice after chloroplast membranes are removed from the juice. The presence of chlorophyll in the juice can be observed by the protein-concentrated juice or isolated protein precipitate having a green or greenish color. The protein-concentrated juice or isolated protein precipitate containing residual chlorophyll is slightly greenish, whereas the protein-concentrated juice or isolated protein precipitate containing trace amount or no chlorophyll is colorless to white.

As used herein, the term "reducing agent" refers to a compound with anti-oxidant function. The terms reducing agent and anti-oxidant are therefore interchangeable in the context of this invention. The examples of reducing agents are Lithium aluminium hydride ($LiAlH_4$), Nascent (atomic) hydrogen, Sodium amalgam, Sodium borohydride ($NaBH_4$), compounds containing the $Sn^{2+}$ ion, such as tin(II) chloride, Sulfite compounds, Hydrazine, Zinc-mercury amalgam (Zn (Hg)), Diisobutylaluminum hydride (DIBAH), Lindlar catalyst, Oxalic acid ($C_2H_2O_4$), Formic acid (HCOOH), Ascorbic acid ($C_6H_8O_6$), Phosphites, hypophosphites, phosphorous acid, Dithiothreitol (DTT), and compounds containing the $Fe^{2+}$ ion, such as iron(II) sulfate, metal hydrides such as NaH, $CaH_2$, and $LiAlH_4$, active metals such as sodium, magnesium, aluminium and zinc, ADH, alcohol dehydrogenase, Boranes, catecholborane, Carrots, copper hydride, copper (low valent), chromium (low valent), Daucus Carota, decaborane, DIBAL-H, diborane, diethyl 1,4-dihydro-2,6-dimethyl-3,5-pyridinedicarboxylate, diisobutylaluminium hydride, diisopropylaminoborane, dimethylsulfide borane, DMSB, Fe, formaldehyde, Hantzsch ester, hydrogen, indium (low valent), iron, isopropanol, LAH, lithium, lithium aluminum hydride, lithium tetrahydridoaluminate, magnesium, manganese, 3-mercaptopropionic acid, 3-MPA, NBSH, Neodymium (low valent), nickel, nickel borohydride, niobium (low valent), 2-nitrobenzenesulfonylhydrazide, phenylsilane, phosphorous acid, pinacolborane, PMHS, polymethylhydrosiloxane, potassium, potassium iodide, 2-propanol, Red-Al, Rongalite, samarium (low valent), silanes, sodium, sodium bis (2-methoxyethoxy)aluminumhydride, sodium borohydride, sodium cyanoborohydride, sodium dithionite, sodium hydrosulfite, sodium hydroxymethanesulfinate, sodium tetrahydroborate, sodium triacetoxyborohydride, strontium, tetramethyldisiloxane, tin hydrides, titanium (low valent), TMDSO, tributylstannane, tributyltin hydride, trichlorosilane, triethylphosphine, trimethylphoshpine, triphenylphosphine, triphenylphosphite, triethylsilane, tris(trimethylsilyl) silane, and TTMSS. Preferably, the reducing agent is food-grade.

As used herein, the term "chelating agent" refers to that a compound which has two or more separate coordinate bonds between a polydentate ligand and a single central atom. Usually these ligands are organic compounds. The chelating agent can bind to a substrate and form a stable chelating complex. The examples of the chelating agent are chloride, cyanide, several organic acids (citric, glycolic, lactic, malic, malonic, oxalic and succinic acids). Deferoxamine, Deferiprone, Deferasirox, Penicillamine, honey, sodium pyrophosphate, sodium hexametaphosphate, sporix, BAL, EDTA (Dexrazoxane), Prussian blue, ALA, BAPTA, DTPA, DMPS, DMSA, EGTA, ribose, deoxyribose, glucose, fructose, glucosamine, sucrose, lactose, maltose, cellulose, starch, pectins, gums, alginic acid, chitin, chitsans, lactic acid, pyruvic acid, citric acid, acetic acid, lipids, monoglyceride, diglyceride, triglyceride, phosphyatidylcholine, phosphatidylethanolamine, ceramide, sphingomyelin, xanthophylls, vitamin A, cortisone, cortisole, cholic acid, deoxycholic acid, taurocholic acid, glycine, alanine, valine, leucine, isoleucine, phenylalanine, tryptophan, serine, threonine, tyrosine, aspartic acid, glutamic acid, lysine, arginine, asp aragine, glutamine, histidine, cysteine, methionine, proline, histamine, adrenaline, insuline, ATP, NAD, FMN, FAD, Coenzyme A, DNA, RNA, carbonate, bicarbonate, cyanides, glycolic acid, oxalic acid, lactic acid, citric acid, orthophosphates, pyrophosphates, metaphosphates, polyphosphates, phytic acid, MDP, HMDP, HEDP, hemoglobin, chlorophyll, plant alkaloids, anthocyanins, tannins, sulfates, sulfonic acids, chondroitin sulfates, vitamin B12, ascorbic acid, and water. Preferably, the chelating agent is food-grade.

As used herein, the term "buffering agent" refers to that a weak acid or base used to maintain the pH of a solution or a juice near a chosen value after the addition of another acid or base. The use of a buffering agent can stabilize the solution or juice at a chosen pH rather than increase or decrease dramatically after the addition of a strong acid of alkali. Examples of a buffering agent are all salt combinations of a cation, such as sodium, potassium, ammonium, or magnesium, with a multivalent anion such as cis-aconitate, citrate, isocitrate, phosphate, sulphate, succinate, sodium or potassium-acetate, 3-{[tris(hydroxymethyl)methyl]amino}propanesulfonic acid, N,N-bis(2-hydroxyethyl)glycine, tris(hydroxymethyl)methylamine, N-tris(hydroxymethyl)methylglycine, 3-[N-Tris(hydroxymethyl)methylamino]-2-hydroxypropanesulfonic Acid, 4-2-hydroxyethyl-1-piperazineethanesulfonic acid, 2-{[tris(hydroxymethyl)methyl]amino}ethanesulfonic acid, 3-(N-morpholino)propanesulfonic acid, piperazine-N,N'-bis(2-ethanesulfonic acid), dimethylarsinic acid, saline sodium citrate, 2-(N-morpholino)ethanesulfonic acid, MES, ADA, PIPES, ACES, cholamine chloride, BES, TES, HEPES, acetaminoglycine, tricine, glycinamide, ammonium carbonate, and Bicine. Preferably, the buffering agent used in the present application is food-grade. Sodium or potassium phosphate are excellent salt additives, as they stabilize proteins; increase solubility; and have a buffering effect. Still preferably, a buffering agent is a concentration of 70 mM of a $Na_2HPO_4$—$KH_2PO_4$ buffer system.

As used herein, the term "mechanically homogenized" refers to that a plant material is homogenized or pulped into a juice by a device in order to break up a tissue of a plant. Preferably, the device for homogenization is a blender, a mixer, a presser, a squeezer, an ultrasonic device, a tissue disruptor. More preferably, the device is a screw pressing homogenizer which can separate leaf juice and insoluble leaf fibers in one step.

As used herein, the term "rapid" refers to a short period of time. Preferably, the period of time is equal to or less than 20 minutes. Still preferably, the period of time is in the range of 1-15 minutes, preferably in the range of 1-10 minutes, preferably in the range of 1-5 minutes, preferably in the range of 1-3 minutes, still preferably in the range of 30 seconds to 1 minute, and even still preferably in the range 0-10 seconds.

As used herein, the term "hydrophobic adsorption" refers to a process by which compounds are adhered to the surface of substances that lack an affinity for water, and tend to repel and not absorb water and also do not dissolve in or mix with water.

As used herein, the terms "polyphenol" and "phenolic compounds" are interchangeable herein, and refer to that a natural, synthetic, or semi-synthetic organic compound. This compound is characterized in having one or more phenol structural units. The number and characteristics of these phenol structural units underlie the unique physical, chemical, and biological properties of the compound. The most abundant polyphenols can be found in plants, and sometimes the contents of the polyphenols can be up to 50% of the dried weight of plant leaves. Plant polyphenols have antioxidant action and hence may be used in some industries, such as reducing tooth decay. Examples of polyphenols are tannin, phytoalexins, (-)-epicatechin (EC), (-)-epigallocatechin (EGC), (-)-epicatechin-3-gallate (ECF), (-)-epigallocatechin-3-gallate (ECGC), proanthocyanidins. flavonols, and fravan-3-ols. Polyphenol content of a protein of the present invention is typically less than 10%, preferably less than 5%, 2%, 1%, 0.5%, or 0.1%, based on the total dry weight of the protein.

As used herein, the term "the chlorophyll-containing membranes" refers to that the membrane of an organelle in a plant cell in which chlorophyll is contained. The chlorophyll-containing membranes can be the chloroplast membranes, or thylakoid membranes.

As used herein, the term "wt %" refers to the weight of a dried or wet mass fraction.

As used herein, the term "time" refers to the timespan of the process, especially during the first steps after cell disruption, is of great importance. Prolonged process time increases the possibilities of the binding of the protein of interest to polyphenols, or the chances that proteases might digest the protein of interest. Therefore it is advantageous to speed up the process steps and to reduce the time between process operations. Preferably, the method of the invention is performed in about 1 day.

As used herein, the term "temperature" refers to the temperature during any process step, and in-between process steps. The temperature in a method of the invention is preferably kept low (close to zero) during the process to maximize the yield of the protein of interest and maintain functionality. A low temperature reduces structural loss caused by denaturation, microbial degradation and protease and polyphenoloxidase (PPO) activity.

As used herein, the terms "pH" and "pH value" refers to the acidity during any process step, and in-between process steps. The pH is preferably optimized for different purification steps and adjusted to the actual content (presence of impurities) in a process stream or a juice. The optimum pH may depend on the protein source, but will generally between pH 6-8 which is the initial chloroplast stroma pH. A high pH value is to be avoided for the following advantages: to minimize covalent binding of polyphenols to the protein of interest, and to prevent association of the protein of interest to the chloroplast and/or thylakoid membranes.

As used herein, the term "ionic strength" refers in particular the amount or concentration of lyotropic salts which can stabilize the hydrophobic interactions within proteins, and keep the proteins structurally intact. Cations that stabilize proteins are $K^+$, $Na^-$, and $NH_4^+$. Anions with the stabilizing function are $H_xPO_1$, $SO_1^{2-}$, $H_x$— citrate, and Cl—. When the concentration of lyotropic salts increases (from zero), protein solubility increases (salting-in). However, when the salt concentration is too high, protein solubility decreases (salting-out).

DESCRIPTION OF THE PREFERRED EMBODIMENTS

The following description is presented to enable any skilled person to make and use this invention, and is provided in the context of particular applications of this invention and their requirements. Various modifications to the disclosed embodiments will be readily apparent to the skilled person and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Harvesting Plant Materials and Storage Thereof

The present invention is directed to a method for obtaining proteins from plant materials. In order to demonstrate the present invention, Rubisco is used as an exemplary protein to be isolated from sugar beet leaves. Hence, the reference to Rubisco hereunder should be interpreted as referring to any plant protein of interest, and where soluble protein is referred to, the preferred embodiment is Rubisco, as this protein forms the bulk of the soluble proteins in plant cells.

Rubisco is an enzyme that is responsible for catalysis of the rate-limiting step in photosynthesis. Rubisco catalyzes the fixation of $CO_2$ by converting it together with ribulose-1,5-diphosphate into two molecules of 2-phosphoglyceric acid. Rubisco present in sugar beet leaves (form I,±530 kDa) consists of eight "large" subunits (53 kDa) coupled to eight "small" subunits (14 kDa). Rubisco possesses a compact tightly three-dimensional structure typical for globular proteins. Due to the amino acid composition of Rubisco, Rubisco is mildly acidic and carries a negative charge at neutral pH. The isoelectric point of Rubisco is around pH 4.5. The solubility of Rubisco is good, considering its rather high hydrophobicity. Rubisco is located in the stroma of the chloroplast at concentrations up to about 300 mg/ml in vivo in plant material.

The Rubisco content is highest in young leaves and decreases during the life time. Hence, with respect to protein yield obtained by use of a process of the present invention, the time of harvesting is critical. Under optimal conditions, in C3 plants, up to 50% of the proteins in leaves is Rubisco. The Rubisco content in stems is reported to be lower. Hence, it is suitably to cut off the stems before processing the leaves since the stems increase the process stream volumes, impurity content, and the need for additives.

It is preferred that the plant materials are harvested essentially undamaged or intact. This is beneficial in order to avoid as much as possible the undesired oxidation of polyphenols and/or plant proteins by polyphenol oxidase in the plant materials, which would deteriorate or negatively influence the yield and/or quality of the protein of interest. The use of undamaged or intact harvested plant materials in methods of this invention thereby has the concomitant advantage that less reducing agents are needed. The undesired oxidation processes start immediately after disrupting cells of plant materials for obtaining the plant juice. Hence, in a method for isolating a soluble plant protein from a plant material according to this invention, the plant material is preferably harvested, transported and stored intact prior to the step of mechanical disruption.

During the harvesting, transport and/or storage process, it is important that the transit time of the plant materials and proteins as short as possible, and that the processes preferably take place at low temperature as earlier indicated hereinabove. As a result, the deterioration of the proteins is limited. Suitably, during the process of harvesting, the plant materials are sprayed with a reducing agent (in the present case metabisulfite, preferably in the form of $Na_2S_2O_5$ (sodium metabisulfite), in order to protect the desired protein against polyphenol oxidase activity.

The amount of reducing agent per part of plant material is preferably below 2 wt %, based on the fresh weight of the plant material, more preferably, the amount of reducing agent when in the form of sodium metabisulfite is less than 1.5% w/w based on the fresh weight of the plant material, such as 1% w/w, preferably less than 1%, 0.8%, 0.6%, 0.4%, 0.3% or 0.2% w/w, still more preferably less than 0.1% w/w. The advantage if this low amount of metabisulfite is that the sodium contamination of the final protein product is minimized. Moreover, the yield of the final protein product (amount of protein isolated per amount of fresh weight of plant material) is increased by this reduction in the use of metabisulfite.

After harvesting the plant material, the process of isolating proteins starts immediately or within a short time period, preferably within 0.5-12 hrs, more preferably within 4-8 hrs, still more preferably within 1-2 hrs. Under the circumstances that the process does not start immediately after harvest, plant materials can be stored at a temperature close to but above 0° C. Extreme (high or denaturing) temperatures can damage the proteins. Ice crystals may damage the cells in the plant materials, and cause mixing of the components in the cells, and further decrease the yield of soluble proteins, such as soluble Rubisco. For example, freeze-drying of soy bean leaves before the process can result in the decrease of the Rubisco yield. Moreover, storage of leaves can decrease the efficacy of heat-induced precipitation of chloroplast membranes.

Disrupting Cells of Plant Materials

For leaves, such as beet leaves that are relatively low in fiber, cell disruption is suitably achieved by mechanical homogenization. A screw press homogenizer is found to be efficient for separating the soluble and the insoluble components of leaves in one single step. The use of the homogenizer reduces the time that Rubisco may attach to the leaves, and also converts the leaves into a juice with a dry matter content of up to 10 wt % based on the total weight of the juice. The dry matter refers in later steps of the extraction process to the content of the protein of interest. In the present example, Rubisco.

Suitably, an extraction buffer can be added to the juice before, during, or after the homogenization step. Depending on the types of homogenization, addition of the extraction buffer afterwards is preferred to decrease the amount of foam. The extraction buffer may also be added to the plant material just prior to or after harvest. The term extraction buffer as used herein includes reference to an extraction solution not containing a buffering agent, hence the term is not intended to be limiting. An extraction buffer comprises at least one of: a buffering agent (e.g. phosphate buffer), a reducing agent (e.g. metabisulfite), and a divalent ion (CaCl2).

In some embodiments of the present invention wherein screw press homogenization is used, a large amount of foam may be generated. Foam formation may result in unfolding of protein so that polyphenols can bind covalently to the protein, which should be avoided. Hence, foam formation is not desired in a process of the present invention. For this, an anti-foaming agent may be added during the homogenization step.

The number and concentration of components in the extraction buffer preferably depends on their effects, price, and whether the components are food-grade. In preferred embodiments the additives are food-grade and comprise reducing agents, metal chelators, and/or buffer salts.

The amount and the concentration of the extraction buffer added before, during or after disrupting the cells to obtain a juice is preferably as low as possible in order to limit production costs of the protein isolate. The concentration of buffering agent used is preferably 50 mM or less. The amount of buffer solution added to the leaves is preferably 50 wt % of the leaves or less.

The juice obtained in the process of disrupting cells is suitably a neutral solution. That means that the pH value of the juice is preferably at about 6-8, more preferably at about 6.5-7.5, and even more preferably at about 7. Such a condition provides advantages to the present invention. First, the solubility of certain proteins, such as Rubisco, is high at this pH, which is a preferred condition because it results in a higher protein yield of the process. Moreover, a higher pH value results in auto-oxidation of polyphenols, and binding of certain proteins, such as Rubisco, to thylakoid membranes, and this should be avoided. Depending on the time span of the step of disrupting cells and the moment of adding the extraction buffer, the pH value of the juice can already be adjusted to the optimal pH value required in the following process step.

The components and concentration of an exemplary extraction buffer is listed in Table. 1.

TABLE 1

The components and concentration thereof in the exemplary extraction buffer. metabisulfite (exemplary reducing agent) and ascorbic acid (exemplary reducing agent) are optional.

| Additive | Concentration |
|---|---|
| Sodium phosphate | 25 mM |
| Metabisulfite | 2% (w/w) |
| Ascorbic acid (vitamin C) | 1 mM |

EDTA as a chelating agent may be used, for instance in an amount of 1 mM in the extraction buffer, but in combination with a step of divalent ion membrane flocculation, EDTA is best omitted. Lysis of the chloroplasts is necessary to liberate certain proteins, such as Rubisco, from the chloroplast stroma into the juice. Homogenization can suitably break the outer membrane of the chloroplasts, while, due to the presence of an inner membrane the chloroplasts remains essentially intact. An extraction buffer can add in this process of lysis of the organelle. The other advantage of adding an extraction buffer to the juice is that a sufficient amount of the extraction buffer with a low osmotic strength can cause the chloroplasts to burst due to osmotic shock. Nonetheless, excessive buffer is cost-prohibitive and results in a diluted juice, which may hinder the effectiveness of the downstream recovery and process for obtain plant proteins from leaves. In exemplary embodiments, a buffer-to-leaf ratio is 0.5 (w/w). Nonetheless, the ratio is not only limited to 0.5 (w/w), and the skilled person can rely on the above teachings to adjust the ratio.

Removal of Chloroplasts and Chlorophyll

Following the disruption of the plant cells, the protein-containing leaf juice (which term is used in general to refer to the plant material juice) is suitably separated from chlorophyll-containing thylakoid membranes of the chloroplast by a heat-, pH and/or divalent ion-induced precipitation, centrifugation, and/or microfiltration of the thylakoid membrane. Preferably, the separation is conducted within 0.1 to 1 hrs after the cells are disrupted.

Thylakoid membrane precipitation can be achieved by moderate heating or using the mild-heat treatment as indicated above, meaning a treatment at about 20-60° C., and suitably for 10-30 minutes, and optionally in combination with a pH value below 7. Fast heating and cooling to the incubation or treatment temperature is preferred in order to optimize the final yield of functional protein. The plant juice is preferably kept in motion (for instance by stirring) during the heating process in order to prevent production of local regions of excessive heating thus preventing the protein from denaturing. The conditions for heat-precipitation may vary with different sources of protein. In the examples described herein for purifying Rubisco from sugar beet leaves, the plant juice was heated to 50° C., for 20 minutes, at pH 6, followed by a rapid cooling to prevent further deterioration of the proteins. A low pH (<pH6 or <pH5, or even <pH4) is not preferred since this may result in co-precipitation of Rubisco with the membranes.

Optionally, the heat-induced thylakoid membrane precipitation can be combined with centrifugation to speed up precipitation of the membranes. Although centrifugation can be used without heating, this is not economical because it requires high centrifugal forces to precipitate the membranes. High speed centrifugation is in most cases less cost effective. Centrifugation at 9000 xg (SLA-3000; Sorval) for 20 minutes at 6° C. is found to be efficient to precipitate the chlorophyll-containing membranes following the above-indicated mild heat-treatment. Although flocculants can in principle be used to improve the precipitation of chloroplast membranes, the addition of flocculants may hinder further application for the chloroplastic fragments, and is therefore not preferred.

The present inventors have now surprisingly found that the addition of a divalent ion to the protein-containing leaf juice greatly enhances the heat-induced precipitation of the thylakoid membranes, thereby effectively removing the chlorophyll from the product. Thus, the present inventors have found that the presence of a divalent ion such as $CaCl_2$ can improve the heat precipitation of chlorophyll-containing membranes, which is advantages in that it improves the yield of the protein isolation process and the overall process speed. In fact, the present inventors have found that the presence of a divalent ion will result in such efficient flocculation of the chlorophyll-containing membranes that precipitation will occur essentially without heating, which greatly improves process yield, and process speed, and reduced process costs.

The effect of the presence of a divalent ion was still further found to allow for a further reduction in the use of reducing agent during the protein extraction process. It was found that divalent ion-induced precipitation (also in combination with heat precipitation) was improved when the amount of reducing agent in the extraction buffer was reduced. The reduction in reducing agent may be to the extent that no reducing agent is present in the extraction buffer. The advantage thereof is that less chemicals are needed, and that process yield and speed are improved. In highly preferred embodiments of this invention the divalent ion-induced precipitation of thylakoid membranes is preferably carried out at low reducing agent concentrations (e.g. less than 0.5% w/w, less than 0.25% w/w, or even less than about 0.1% w/w based on the fresh weight of the plant material), without heating of the plant juice (i.e. maintaining ambient temperature during processing). The preferred divalent ion source is a calcium-salt, most preferably calcium chloride.

Optionally, microfiltration can be combined with the above precipitation treatments to remove the chloroplast membranes. In an exemplary embodiment, microfiltration with 0.45 µm filters is used after membrane precipitation and centrifugation to remove the residual membranes, any remaining chlorophyll, and sterilize the juice. Moreover, in order to prevent particles clogging on the filters, open channel filters are suitably used, in which large particles are allowed to pass through the membrane cassette without blocking the channels, Suitably, the pore size of the filter is 0.20-0.45 µm in order to retain all chlorophyll-containing membranes, bacteria, and/or any possible pathogens. Hence, microfiltration may be beneficial to use in combination as it may provide for a sterilization step. In preferred embodiments of a method of this invention the step of microfiltration is included in order to improve the ultrafiltration processing step. In the absence of the step of microfiltration, which preferably removes particles larger than 0.45 µm, the ultrafilter may be clogged.

When a freshly prepared juice is treated by heat precipitation followed by centrifugation and microfiltration, nearly all chlorophyll-containing membranes can be successfully removed. In contrast to the freshly prepared juice, it can be less easy to remove the chlorophyll-containing membranes from a juice if the juice is stored under low temperature for a considerable period of time, such as for instance for a day. Hence, it is preferred to process the leaves immediately, or essentially directly (on the same day) after harvesting.

Removal of Polyphenols

Polyphenols are an impurity with a negative effect, on the nutritional value and digestibility of plant-obtained proteins. Polyphenols bind to the plant proteins covalently or non-covalently, Non-covalent binding herein refers to hydrophobic interactions and is a reversible binding, whereas covalent binding deprives the proteins of their functionality. There are several methods for removing the non-covalently bound polyphenols. In terms of efficacy and costs, ultrafiltration and/or hydrophobic adsorption are advantageous methods to remove non-covalently bound polyphenols. By means of a hydrophobic adsorption column packed with hydrophobic resin, a majority of phenolic compounds (including polyphenols) can be removed. Moreover, a hydrophobic adsorption column is advantageous as it also removes the residual chlorophyll and many of the remaining undesirable compounds, such as off-flavor-causing compounds or compounds with undesirable color and undesirable smell, including grass-smell and off-flavors. Preferably, the remaining chlorophyll, polyphenol, and off-flavors can be removed by using a hydrophobic adsorption column.

In an exemplary embodiment, an Amberlite XAD16 packed column is used to hydrophobically adsorb and remove polyphenols. At pH value 6 or 8, about two thirds of the total polyphenol content in the juice is removed, including red/brown colored polyphenols. The phenolic compounds adsorbed in the column can be eluted by washing the column with 50% ethanol.

On the other hand, the covalent binding of polyphenols to the protein is irreversible and can be prevented by addition of additives into the leaf juice. Phenolic compounds are converted into o-quinones by polyphenoloxidase (PPO). The formation of o-quinones is disadvantageous because o-quinones easily polymerize with other polyphenols (formation of tannin), or form covalent bonds with proteins, and hence can cross-link proteins. Polymerized polyphenols have a brown color and have larger size, and therefore are more difficult, to separate the polymerized polyphenols from the protein.

Use of reducing agent such as metabisulfite and cysteine can reverse the conversion of phenolic compounds into o-quinones, which otherwise bind to plant proteins covalently. Suitably, PPO inhibitors can also be used to prevent the covalent binding of phenolic compounds to proteins. The suitable PPO inhibitors may depend on plant sources. For example, ascorbic acid can inactivate PPO irreversibly and reduces the oxidized reaction products of PPO. Metal chelators such as EDTA, citric acid and oxalic acid can chelate copper and zinc, and hence inhibit PPO and metalloproteases. All of these compounds that can prevent the negative effects of polyphenols are collectively referred to herein as reducing agents.

Reducing agents (including PPO inhibitors) do not only prevent covalent binding of phenolic compounds to the protein, but also prevent polymerization of phenolic compounds thus keeping the size of phenolic compounds small. Therefore, reducing agents added to the juice simplify the separation of proteins and polyphenols.

Polyphenols are separated from the soluble proteins by both hydrophobic absorption, but primarily by ultrafiltration/diafiltration. While an estimated 25-75% of the total polyphenol content can be removed by ultrafiltration, hydrophobic absorption will completely remove any remaining polyphenol. Experimental results showed that using 30 kDa filters, the bulk of polyphenols can be separated from Rubisco. Furthermore, ultrafiltration is used to concentrate the protein in the process stream (the stream of plant juice to aqueous protein concentrate) and removes small additives such as metabisulfite and salts. In addition, the polyphenols are separated from the protein and are removed via the filter permeate. Once the protein fraction (retentate) from the ultrafiltration is concentrated to a satisfactory level (e.g. 25-50 wt % of protein), it may be washed to further lower the amount of polyphenols and extraction composition additives. In the experiments performed no clogging of a 30 kDa ultrafiltration membrane was observed. Larger condensed polyphenols may be removed by ultrafiltration as well. For this, a 100 kDa ultrafiltration, membrane may be used. Use of ultrafiltration is not limited to the use of these specific molecular weight cut-off sizes. The skilled person will appreciate that the indicated range of about 30-100 kDA will generally work well and further optimization may result in a proper filter for isolation of different proteins from a variety of plant materials in accordance with a process of the present invention using the general rule that the molecular weight cut-off of the membrane should be ⅓rd-⅙th the molecular weight of the protein molecule to be retained.

Thus, ultrafiltration may also be used to concentrate the juice, increase its protein content and remove small compounds such as metabisulfite. Once the desired proteins are concentrated on the ultrafilter, an aqueous solution, preferably buffered, may be used to further dilute and wash away any remaining polyphenol from the retentate comprising an aqueous solution of concentrated proteins.

Optionally, diafiltration is used to wash the proteins in order to remove salts, polyphenols, and/or undesirable compounds from the proteins in the juice. Optionally, an activated carbon can be used to adsorb and remove polyphenols. The advantage of using an activated carbon is low cost and convenient. The disadvantage of this use is that the recycled polyphenols cannot be used in other applications. Diafiltration may be performed as a tangential flow process and is used to enhance either product yield or purity. During diafiltration, buffer is introduced into a recycle tank while filtrate is removed from the unit operation. In processes where the product is in the retentate, such as is the case in the present process, diafiltration washes components out of the product pool into the filtrate, thereby exchanging buffers and reducing the concentration of undesirable molecules and ions. The solution retained by the diafiltration membrane is known as the concentrate or retentate. The solution that passes through the membrane is known as the filtrate or permeate.

Ultrafiltration as indicated herein is used throughout the downstream separation process for the purification of the soluble plant proteins. The specific application of ultrafiltration refers to protein concentration (i.e., volume reduction), desalting, and buffer exchange, all of which are used to condition the product prior to, or immediately after, other separation processes or as part of the final product formulation. Buffer exchange and de-salting are typically performed using a diafiltration mode in which the small impurities and buffer components are effectively washed away from the product by the continuous (or discontinuous) addition of new buffer with the desired composition and purity. The most common approach is to perform the diafiltration using a constant retentate volume. Hence, diafiltration is used herein to refer to a specific mode of ultrafiltration, and the same molecular weight cut-off sizes are applicable. A protein concentrate after ultrafiltration or diafiltration generally will comprise a concentrated protein solution of 25-50 dry wt % of protein based on the total weight of the solution.

Hydrophobic adsorption is an essential element of the present invention because the present inventors have discovered, that residual. chlorophylls, not removed by precipitation and/or microfiltration, the remainder of the polyphenols, and substantially all off-odors may be removed by a single pass over a column comprising a hydrophobic absorption resin. The configuration of using the hydrophobic column is advantageous in that it removes most of the undesirable hard-to remove compounds from a soluble protein-containing plant juice in a single pass, which is extremely efficient for removing these undesired substances and allows the process to be economical.

Hydrophobic adsorption in aspects of this invention comprises the use of a column packed with hydrophobic adsorptive resin. A very suitable resin for capture and simultaneous single pass removal of residual chlorophyll, off-odors and phenolic compounds was found to be a non-ionic crosslinked aromatic polymer resin, preferably a non-ionic crosslinked polystyrene resin, even more preferably a macroreticular styrene-divinylbenzene copolymer matrix. Such resins are commercially available under the names of Amberlite™ XAD-2, Amberlite™ XAD-4 and Amberlite™ XAD-16, Amberlite™ XAD 16N, Amberlite™ XAD 1180N, and Amberlite™ XAD 1600N (Sigma, St Louis, USA). Comparable resins from other suppliers are equally suitable. Amberlite™ XAD-16 is highly preferred as it results in excellent removal of residual chlorophyll, phenolic compounds, and off-odor or off-flavor-causing compounds from the juice. Other suitable and exemplary materials with the function of hydrophobic adsorption are talc, hydrophobized calcium carbonate, hydrophobized bentonite, hydrophobized kaolinite, hydrophobized glass, or a mixture thereof. Many hydrophobic adsorptive materials are commercially available, such as Toyopearl® Butyl-650, Tenax® TA™, Phenyl Sepharose™, Butyl Sepharos™, SOURCE™ 15 ethyl and SOURCE™ 15 phenyl media and Carbograph 1TD™. Preferably, the hydrophobic adsorption is performed by a column packed with hydrophobic adsorptive material, such as in the form of a matrix or beads. Still preferably, the hydrophobic adsorption is performed by using a non-ionic crosslinked polystyrene resin, most preferably Amberlite™ XAD 16 resin, or an equivalent material.

A final product form of the protein can be obtained by drying of the concentrated protein solution, such as freeze drying (lyophilisation or cryodesiccation) and spray drying. The dried protein product can subsequently be applied in for instance food products.

Protein Precipitation

Optionally, protein precipitation can be used to separate Rubisco from polyphenols, proteases, and additives. Protein precipitation is induced by pH or by an increase of the ionic strength. After the protein is precipitated, a pellet wash can be used to remove the remaining soluble impurities from the precipitate. The bulk of polyphenols in the supernatant can be removed by further processes.

Precipitation is suitably performed at pH 4.5 for inexpensive isolation of certain proteins, such as Rubisco. Because of the nature of Rubisco, Rubisco dissolve at higher pH, whereas becomes insoluble at lower pH.

Application of the Plant Proteins

The proteins obtained by the process can be functional, which makes the proteins more valuable than their non-functional counterparts. The proteins can contribute to the structure and texture of a food product. For example, the proteins are suitably used as thickening agents, foaming agents, meat substituents, gelling agents, emulsifier and nutritional supplements. In addition, the proteins as obtained with the present process are competitive in price. Finally, the proteins are produced in a sustainable and environmentally friendly process.

System for Isolating a Soluble Plant Protein

The present invention also pertains to a system for isolating a soluble plant protein, preferably adapted for performing a method of the present invention as described above.

In short, this, preferably mobile, extraction system for extracting functional protein from a plant material may have the form of a self-propelled crop harvester having a header for harvesting crop material, a press for separating the crop material into liquid and fibrous fractions, an optional heater for optionally heating the liquid fraction or a divalent ion source, a separator for separating the heat- or divalent ion-aggregated chlorophyll-containing membranes from the liquid protein fraction, an optional microfilter for preferably removing fractions >0.45 µm (optionally in the form of a sand bed), an ultrafilter for removing polyphenols and a hydrophobic absorption column for removing any remaining impurities from the proteins.

In a preferred embodiment, the protein isolation system according to this invention comprises optional means for harvesting plant material from a crop plant, and at a first proximal end of the system a facility for receiving harvested, preferably waste, plant material. The receiving facility may have the form of a loader mounted on the screw press facility. When loaded into the system, the plant material will be fed to the screw press facility at the inlet at a rate that is preferably controlled or controllable.

During operation of the system, the extraction composition comprising at least one reducing agent flows from the receptacle for the extraction composition and is brought into contact with either: i) the plant material prior to harvesting, ii) the harvested plant material prior to it entering the screw press, iii) the plant material/plant juice mixture during pressing, and/or iv) the plant juice originating from the pressed plant material. In a preferred embodiment, the extraction composition is contacted with the plant material prior to this material entering the screw press facility since the screw press action will provide beneficial distribution and mixing of the extraction composition with the plant material, thereby improving the composition's effectiveness.

The plant juice thus produced at the raw juice outlet is then delivered to a precipitation facility, which may be a heating facility or a flocculation tank having a divalent ion supply. The heating facility may be a common heat exchanger such as one comprising heating coils for heating the juice by means of a heated gas or liquid, or an electrical heating element surrounding a tube delivering the juice from the screw press to the separating/microfiltration facility. The temperature of the juice is controlled for instance by using a feedback control mechanism that operates the electrical heater or controls the flow of the heated gas or liquid through the heat exchanger. This control is such that the juice is heated to a temperature of between about 40° C. to 60° C., and thereby subjected to a mild heat treatment as defined in the method described herein above. The juice is kept at the controlled temperature for mild heat treatment for a period of between 1 minute and 3 hours, or for a period as indicated in the method described above. This may be accomplished by controlling the flow of the juice through the system thereby controlling its residence time in the heat exchanger or by collecting the juice at a holding tank where its temperature is maintained for the desired duration.

Having been subjected to the desired heat treatment, the heated plant juice is then delivered to the cooling facility. This may again be a common heat exchanger such as one comprising cooling coils for cooling the juice by means of a cold gas or liquid or an electrical cooling element based on a thermoelectric heat pump surrounding a tube delivering the juice from the heating facility to the separating/microfiltration facility. The cooling rate of the juice may be controlled for instance by using a feedback control mechanism that operates the electrical cooler or controls the flow of the cooled gas or liquid through the heat exchanger. This control is such that the juice is rapidly cooled to a temperature of between about 1° C. to 15° C. in a time frame of about 1 minute to 1 hour following its entry in the cooling facility. The cooled juice is then preferably kept at the controlled cool temperature for the duration of the protein isolation procedure as indicated in the method described above.

The heated and subsequently cooled plant juice, or, alternatively or in combination therewith, a divalent ion-induced precipitation of the thylakoid membranes in a flocculation tank (wherein the divalent ion is provided in an amount that results in flocculation of the chlorophyll membranes) is then delivered to a separation facility for separating the slurry into a solids component stream comprising aggregated chloroplast membranes with chlorophyll, and a soluble protein stream including water and soluble protein and having a reduced chlorophyll content compared to the raw plant juice. The separation facility (also referred to herein as the precipitation unit and/or microfiltration unit depending on its position in the process) ensures separation of heat- or divalent ion-aggregated solids from plant juice thereby providing a product stream flowing from the separation facility outlet and comprising the soluble plant protein of interest and having reduced chlorophyll content compared to the raw plant juice. The rate of delivery of the heated and subsequently cooled plant juice, or of the divalent ion-flocculated juice, to the separation facility is preferably controlled such that the rate of the product flow of soluble plant protein exiting the final unit of the separation facility (e.g. the microfiltration unit) matches the flow capacity of the ultrafiltration facility to which the product stream is delivered.

The soluble protein stream exiting the separation facility is then delivered to an ultrafiltration facility, which ultrafiltration facility preferably has the form of a diafiltration setup using for instance a tangential flow filtration unit. The pressure and temperature in the ultrafiltration facility are preferably controlled to optimize separation of polyphenols via the filtrate, while the soluble protein is retained at the retentate. In a process of the present invention, the diafiltration step washes polyphenols and other undesirable components out of the soluble protein product pool into the filtrate. Washing includes exchanging buffers in ways known to one of skill in the art and the process reduces the concentration of undesirable components in the retentate. The addition of buffer solutions (which may be ordinary tap water or dedicated food-grade buffer systems at pH values referred to in the method as described above) to the ultrafiltration retentate facility is preferably controlled at a rate that the referred washing is optimized, while the soluble protein is concentrated in the retentate to provide a soluble protein enriched plant juice concentrate having reduced polyphenol content compared to the raw plant juice. Such a concentration of the protein in a smaller volume is beneficial in order to reduce costs associated with delivery of the concentrated protein stream to the hydrophobic adsorption column, in particular in the case that the system is split in a mobile and fixed part as described herein below. Preferred embodiments relating to the method of this invention as described herein above also give rise to preferred embodiments in this aspect of the invention. For instance, the ultrafiltration facility is suitably equipped with an ultrafilter membrane having a molecular size cut-off in the range of about 20-100 kDa, depending on the size of the soluble protein to be isolated as described in the method herein above, and the concentration of the protein in the soluble protein enriched plant juice concentrate obtained after ultrafiltration is indicated therein as well.

The delivery of the plant juice in its various stages of processing from the screw press outlet to the ultrafiltration facility is ensured by means of one or more pumps incorporated in the system. The skilled person will readily design a configuration of the various processing facilities and pumps to achieve continuous supply or supply in metered quantities from the outlet of one facility or unit to the next facility or unit in the system. One possible configuration is provided in FIGS. 3 and 4.

Figure 3:
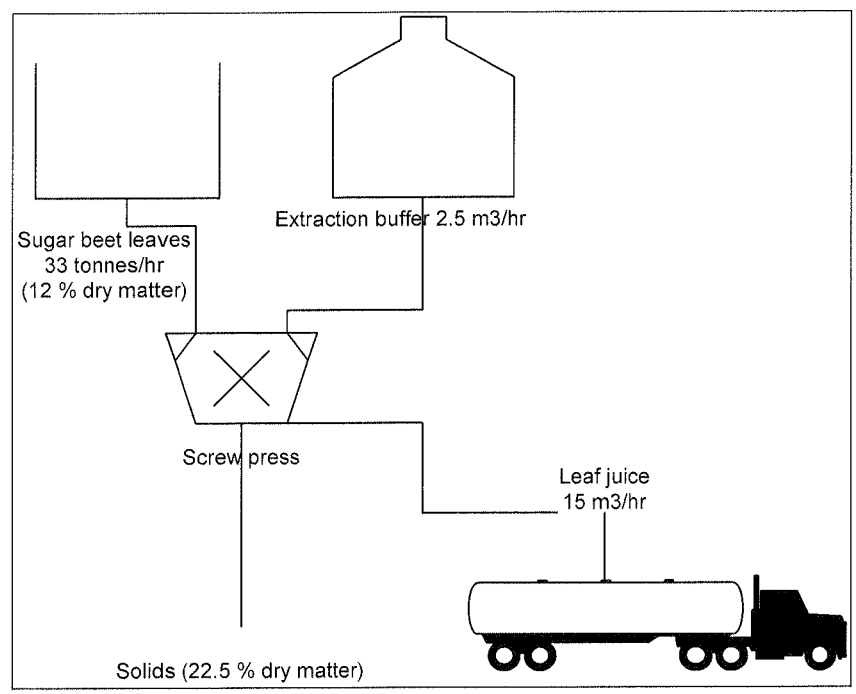
FIG. 3 shows the schematic display of the production of plant material juice on a farm.
Figure 4A:
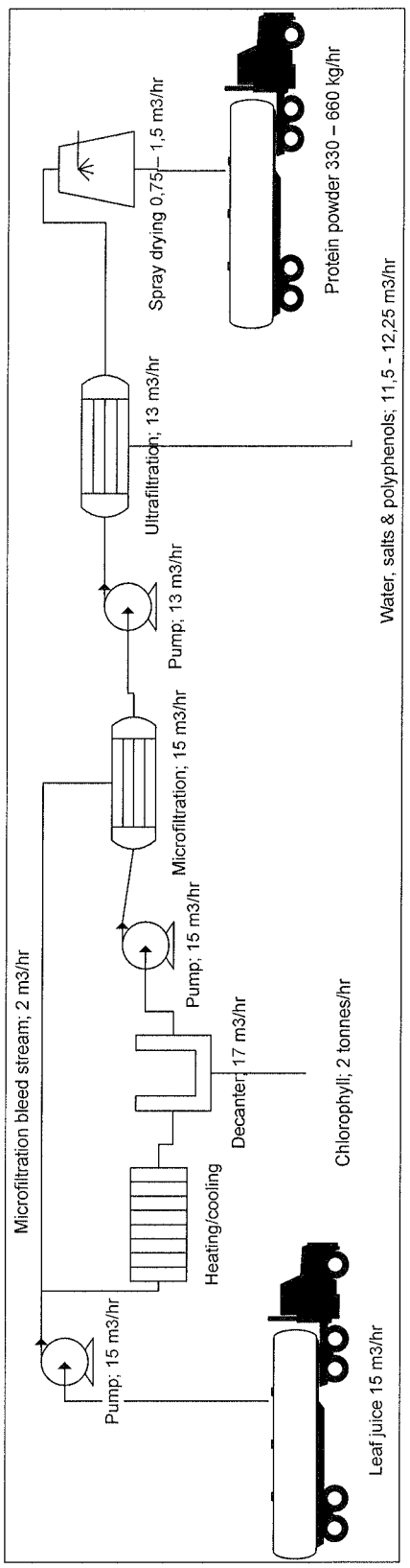
FIG. 4 shows the schematic display of the production of protein from plant material juice at a separate off-farm location, wherein FIG. 4A provides a comparative installation lacking the simultaneous single pass removal of residual chlorophylls, polyphenols and off-odours.
FIG. 4B depicts an installation according to this invention.
Figure 4B:
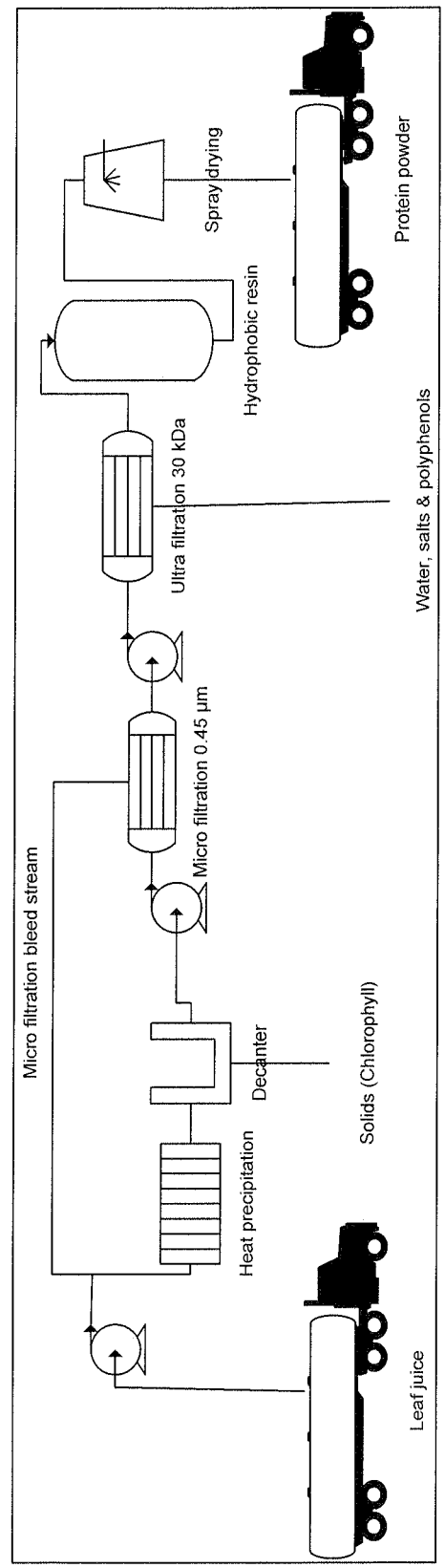
Figure 5A:
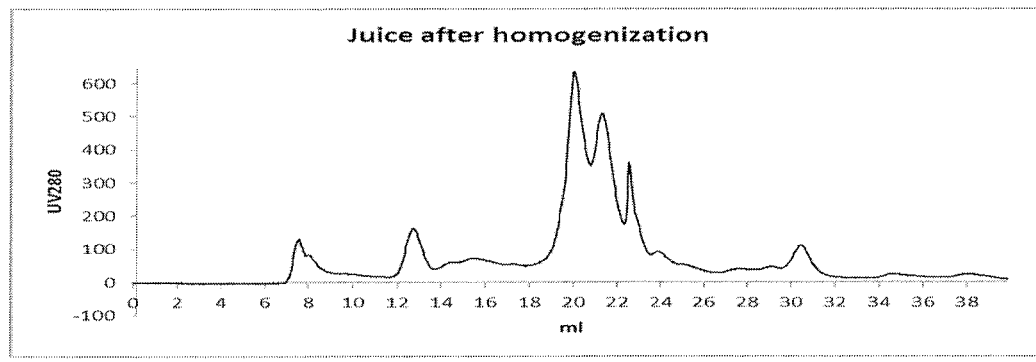
FIGS. 5A-5E show the analysis result of Superdex 200 chromatogram (size exclusion) of homogenized juice, microfiltrated juice, XAD16 fraction 4, XAD16 fraction 9, and XAD16 fraction 25.
Figure 5B:
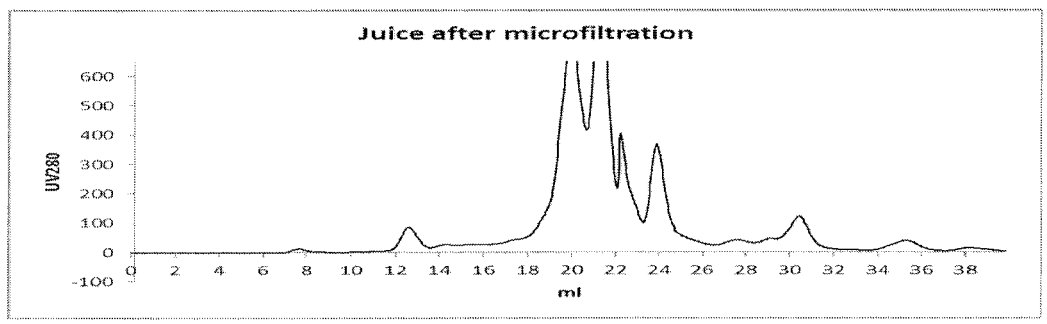
Figure 5C:
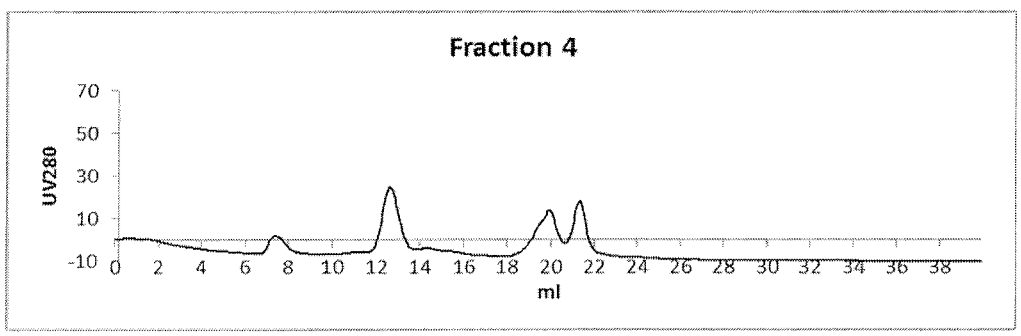
Figure 5D:
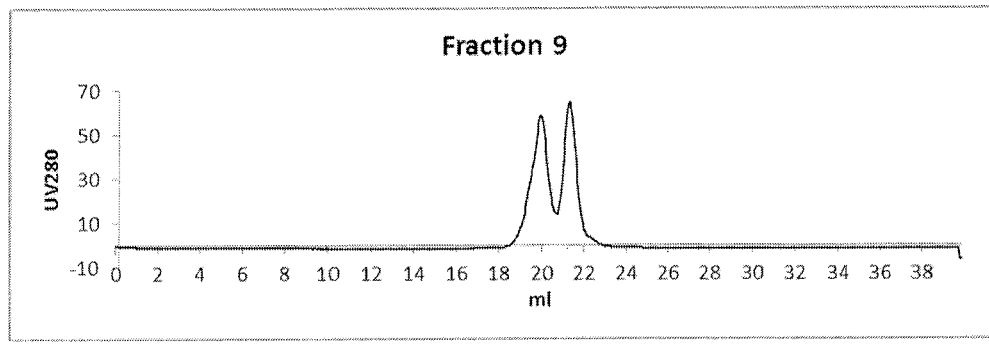
Figure 5E:
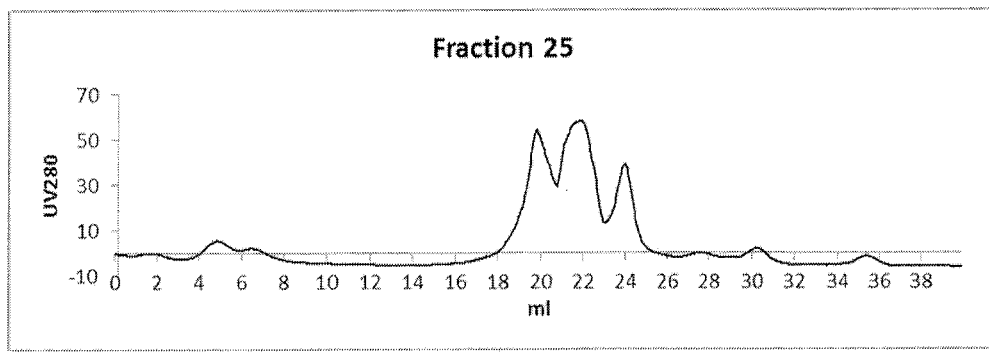

Preferably, the system is operational at a material processing rate as indicated in FIGS. 3 and 4. It must be noted that the plant juice exiting the screw press in FIG. 3 may directly enter the separation facility of FIG. 4 (A or B). As indicated in FIG. 3, a plant material input rate of about 33 tons/hr will in the case of sugar beet leaves result in a combined extraction buffer/plant juice stream of about 15 m$^3$/hr when allowing a screw press solids outflow having a dry matter content of 22.5 wt. %. This stream of treated plant juice (raw plant juice having added thereto the extraction buffer optionally comprising the reducing agent) flows through the precipitation facilities (heating and cooling facilities, or divalent ion flocculation facility) and is then fed into the separation facility, which in the case of FIG. 4 comprises both a decanter and a microfiltration unit in serial configuration. In a preferred embodiment as indicated in FIG. 4A, a bleed stream exiting the microfiltration unit at a rate of about 2 m³/hr is mixed with the stream of treated plant juice prior to it entering the precipitation facilities. This results in a stream entering the separation facility at the level of the decanter (or any other suitable sedimentation unit) of about 17 m³/hr. Allowing for a removal rate of aggregated chlorophyll of about 2 tonnes/hr, the steam entering the microfiltration unit is maintained at about 15 m³/hr using the bleed stream to maintain the mass processing rate through the separation facility at the level at which juice is produced. The rate at which the process stream subsequently enters the optional microfiltration facility and thereafter the ultrafiltration facility (which may be reduced as a result of the bleed stream) produces a filtrate (waste) stream that is about 85-95 wt % of the retentate protein product stream. The ultrafiltration filtrate stream in this example may reach 11.5-12.25 m³/hr, while the retentate protein product stream may be in the order of 0.75-2.5 m³/hr. Although FIG. 4A provides a schematic drawing of a comparative installation, without the hydrophobic adsorption facility feature of the present invention, it illustrates very suitably the product flows applicable in aspects of this invention.

The system of the present invention further comprises a hydrophobic adsorption facility (FIG. 4B) comprising at least one column packed with a hydrophobic adsorptive resin, preferably a non-ionic crosslinked polystyrene resin. The hydrophobic adsorption facility is located between the ultrafiltration facility and the drying facility, and the complete retentate protein product stream of 0.75-1.5 m³/hr exiting the ultrafiltration unit is loaded onto the hydrophobic adsorption column. This chromatography column system may be composed of a single column, but is preferably plurality of columns each receiving a portion of the retentate protein product stream. The columns may also be arranged such that one or more columns are in use for separation and receive an ultrafiltration retentate stream, while one or more other columns are in the process of being regenerated and receive an ethanol eluent to clean the column. A series of valves may be used to switch the process streams between active and regeneration phase columns.

Preferred embodiments of the hydrophobic adsorption resin are similar to those used in the method described herein above. The soluble protein is separated from polyphenols, chlorophyll and off-odors by a single pass over the hydrophobic adsorption column(s), whereby the soluble protein essentially passes through the column without being adsorbed, and elutes earlier than the small molecule polyphenols, chlorophyll and off-odors through the phenomenon of size exclusion. In addition, polyphenols, chlorophyll and off-odors are retained by either hydrophobic adsorption or exhibit reduced migration through the column as a result of escaping the size exclusion effect. Rubisco for example will not be retained by size-exclusion on a column with XAD16 resin. A skilled person will appreciate that suitable other columns may be selected and used based on the insight obtained by the present inventors and disclosed herein. The protein-enriched eluent that elutes from the hydrophobic adsorption column is suitable for further processing. This eluent may be obtained as discrete fractions, or as a single pass eluent. Preferred systems include those that comprise means for constant monitoring of the protein content in the eluent, and that discontinue the product stream when polyphenols, chlorophyll and/or off-odors start permeating through the column and start eluting from the column. A product stream of 0.75-1.5 m³/hr exiting the hydrophobic adsorption column may be attained.

The system of the present invention further preferably includes a drying facility for drying the column permeate. Spray drying allows for the processing of the column permeate product stream of 0.75-1.5 m³/hr to yield a protein powder at a rate of 330-660 kg/hr.

A system for isolating a soluble plant protein according to this invention has the potential to double the profit from a crop production areal. The proteins are of high purity and food-grade.

The system of the present invention is preferably mobile in that at least the screw press facility, the precipitation facility, the separation facility, the optional microfiltration facility, and the ultrafiltration facility can preferably move with a crop-harvesting machine at a crop harvesting site, however, it is also contemplated that the system can be retrofitted to existing fixed facilities to improve the operational efficiency of such fixed facilities. Both the hydrophobic adsorption facility and the drying facility may also be mobile with the remainder of the system, but are preferably part of a separate fixed facility, where the concentrated ultrafiltration retentate protein product stream is processed.

The invention will now be illustrated by the following, non limiting examples.

EXAMPLES

Example 1

Isolation of Rubisco on Industrial Scale

In this experiment, a method for obtaining Rubisco from sugar beet leaves in industrial scale is illustrated. The complete process is illustrated in FIG. 1.

About 100 m² sugar beet leaves are collected mechanically from a test farm. Harvesting of stems is avoided. The leaves are disrupted and pressed at a screw press, resulting in solids separation from the leaf juice. The juice is transported to the pilot facility at TNO in Zeist for further purification. The process is summarized in Table 2.

An amount of 3.000 kg of sugar beet leave juice is collected. Impurities such as brown leaves and occasional stems are removed. 100 litres extraction buffer is added to the leaf juice, containing 30% Sodium Metabisulfite at a pH of 6.0.

Subsequently, heat-induced thylakoid membrane precipitation is performed by using two heat exchangers, one for heating and one for cooling the juice. The juice was rapidly heated to 50° C. in the first heat exchanger. A piping system with specific volume is used to realize the required retention time of 20 minutes. Cooling of the juice below 20° C. is subsequently performed with the second heat exchanger.

Precipitated membranes are removed by centrifugation with a decanter centrifuge in order to remove the sediment material. A separator centrifuge is subsequently used to remove the remaining suspended solids from the juice to obtain a clear, brown liquid.

Ultrafiltration with a ceramic 150 kD cut off membrane is used to concentrate the 3,000 kg of juice by a factor of 15. The remaining 200 kg of juice is thafiltrated for a total of 3 times with a 1 to 1 ratio to obtain a low salt concentration in the protein concentrate. The protein concentrate has a protein concentration of 20% and has a brown colour.

Hydrophobic adsorption is used to remove the phenolic components and off-flavours from the concentrate. The juice is pumped through a column filled with a volume of 10 litres of Amberlite XAD-16 resin (Rohm and Haas Company, Philadelphia, U.S.A). The result is a light yellow protein solution.

The concentrate is spray-dried at a rate of 10 litres per hour. An amount of 40 kg of dry protein product was produced. The product is a white, odourless and tasteless powder, consisting of 95% pure protein, essentially Rubisco.

TABLE 2

Summary of the industrial scale experiment of obtaining Rubisco from sugar beet leaves

| # | Operation | Equipment | Removed compound |
|---|---|---|---|
| 1 | Harvesting | Beet combine harvester | Leaves without stems |
| 2 | Pressing | Screw press | Solids |
| 3 | Heating (50° C., 20 min) | Heat exchangers | — |
| 4 | Decanter centrifugation | Westfalia Decanter | Sedimented components |
| 5 | Separator centrifugation | Westfalia separator | Suspended solids |
| 6 | Ultra filtration | Ceramic tubular membrane 150 kD | Water, polyphenols and salts |
| 7 | Hydrophobic adsoprption | Amberlite XAD-16 resin | Polyphenols, off-flavours |
| 8 | Spray drying | Spray dryer | Water |

Example 2

Spectrophotometer and Superdex 200 Analysis of the Performance of Amberlite XAD16 Packed Column on Removal of Polyphenols Samples with a volume of 200 µl were analyzed on a size-exclusion chromatography column (Superdex 200) with a buffer containing 25 mM Tris/HCL 200 mM NaCl @ pH 8. Larger components elute faster and were detected more to the left of the chromatogram. Samples were diluted at a 1:1 ratio (v/v) with a 50 mM Tris/HCl 400 mM NaCl pH 8 buffer and filtrated (0.45 µm) before analysis on the Superdex 200. The sample volume was 200 µl for all samples. Samples were stored at 6° C. before analysis.

The sample "Juice after homogenization" was first centrifuged (13,500 rpm, 5 min, no temperature regulation) before it was diluted and filtrated. This sample was obtained from freshly-harvested sugar beet leaf juice.

Peaks were identified in FIGS. 5A-E. The first of the relevant peaks was at 7.4-7.9 ml, identified as large material (LM), probably thylakoid membrane protein complexes containing chlorophyll, DNA or aggregated Rubisco. The second relevant peak was at 12.2-12.7 ml, identified as structurally intact and free Rubisco. The third and fourth relevant peaks were at 19-20 ml (large polyphenol) and 21-22 ml (small polyphenol), and were assumed to be two of the main polyphenol size classes.

From the chromatograms of the juice after homogenization and the processed juice after microfiltration, it was observed that several large components which were located around the Rubisco peak (±12.5 ml) were removed by the heat precipitation. These components make it difficult to estimate the actual Rubisco content in the juice after homogenization, and to compare actual Rubisco content with the Rubisco content after the heat precipitation. However, it was expected that a portion of Rubisco is lost because of the heat precipitation step, as the peaks for Rubisco from FIG. 5B differ in height (162 vs 86 mAU) and area (170 vs 88 mAU ml) as calculated by the UNICORN software (zero baseline).

Fractions 4, 9 and 25 obtained from the XAD 16 column were also analysed on the Superdex 200 column to show which components were present in the fractions. Fraction 4 contains Rubisco, some larger (probably chlorophyll-containing) material (7.42 ml) and also some polyphenols. The Rubisco peak was not tailed to the left, indicating that there was no aggregation of Rubisco. Fraction 9 contains polyphenols that do not interact strongly with the XAD16 resin. These polyphenols were eluted later because of the size-exclusion effect of the XAD16 resin. Rubisco from sugar beet leaf has a molecular weight of ±530 kD, while the pore size of the XAD16 is ±250 kD. Rubisco was therefore not retained by size-exclusion on XAD 16. The smaller polyphenols were expected to be retained by size-exclusion and probably also by hydrophobic interaction with the XAD 16 resin because of the width of the second peak on the XAD 16 chromatogram. Fraction 25 is eluted with 50% ethanol, and contains the main polyphenols and several smaller components. It was expected that these components strongly interact with the XAD16 column and cannot be removed by elution with 25 mM sodium phosphate buffer pH 6. It was striking that in all three fractions analyzed, the ratio's of the small and the large polyphenol peak were similar. It seems that whether a polyphenol is strongly adsorbed is not related to its size, but would rather be related to structural features that are at the same time responsible for polyphenol color.

TABLE 3

Description of the Superdex 200 samples and Figure references

| Sample description | FIG. |
|---|---|
| Juice after homogenization | 5A |
| Juice after microfiltration | 5B |
| XAD16 fraction 4 | 5C |
| XAD16 fraction 9 | 5D |
| XAD16 fraction 25 | 5E |

Figure 6A:
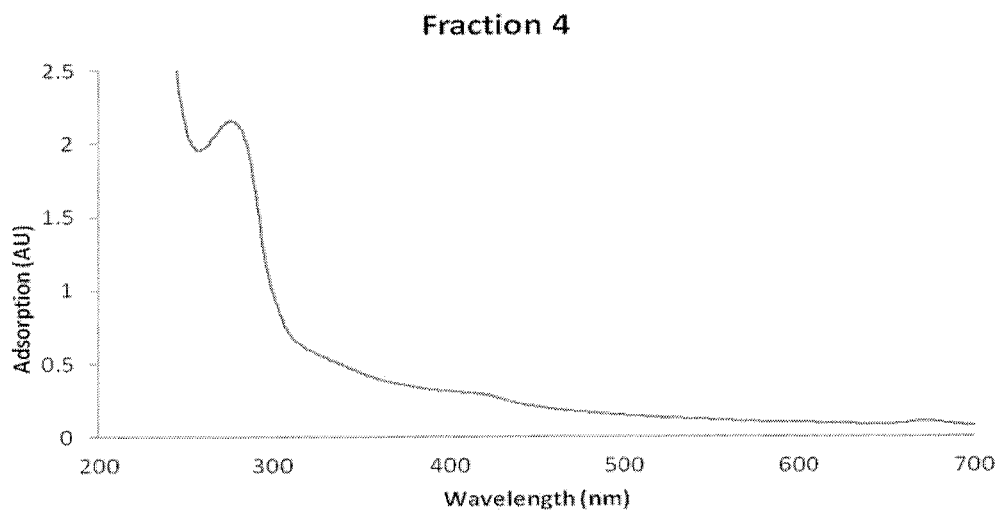
FIGS. 6A-6C show the spectrophotometer analysis of homogenized juice, microfiltrated juice, XAD16 fraction 4, XAD16 fraction 9, and XAD16 fraction 25.
Figure 6B:
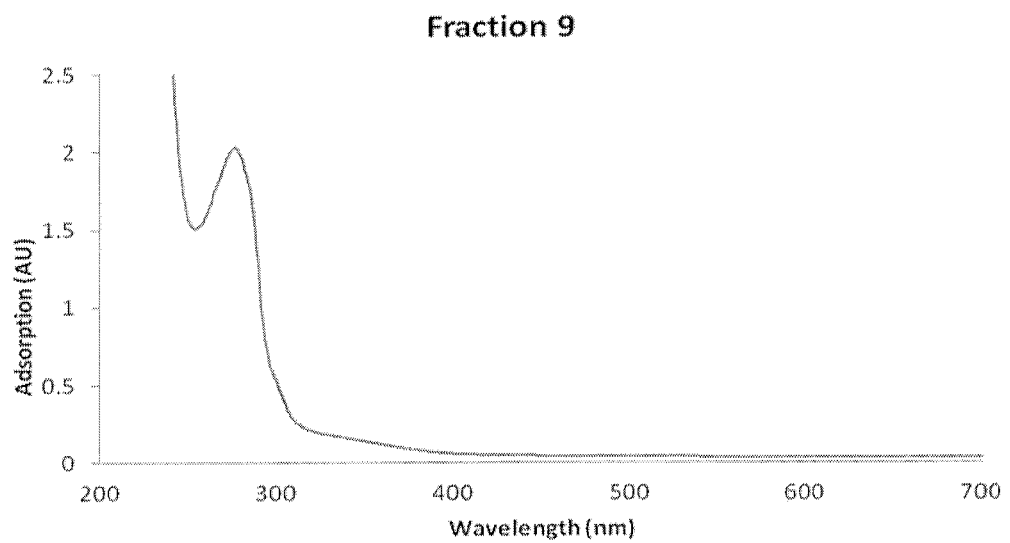
Figure 6C:
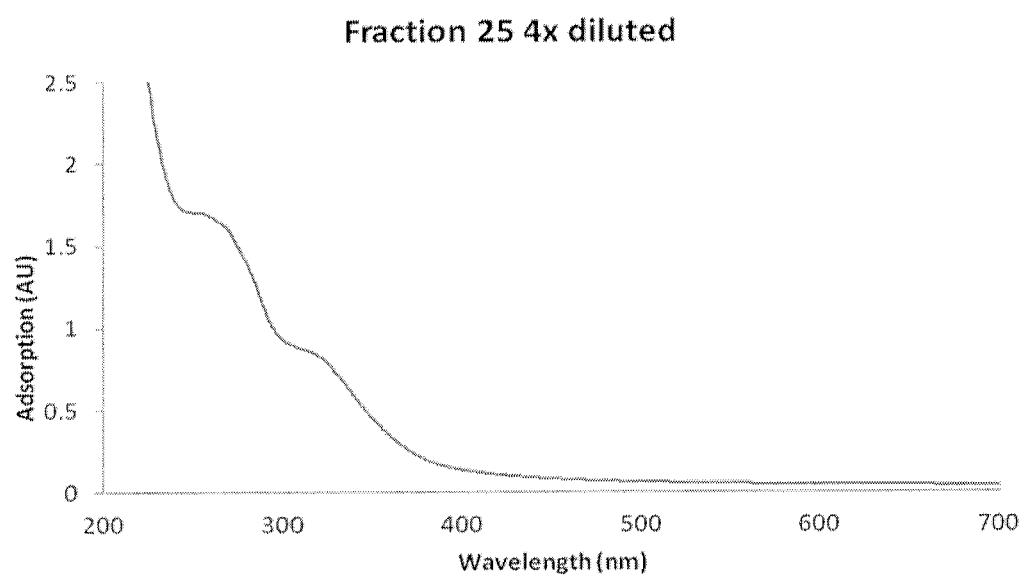

Moreover, the samples of fraction 4, 9 and 25 were analysed using a UV/Vis spectrophotometer. The results are shown in FIGS. 6A-6C. The spectrum of fraction 4 showed a peak maximum at 276 nm, which could be attributed to the mixture of Rubisco and polyphenols. Also, there was increased adsorption around 410 nm and a small peak at 672 nm, both characteristic for chlorophyll. The spectrum of fraction 9 shows a peak maximum at 276 nm, due to the presence of polyphenols. No increased adsorption at other wavelengths was obtained. For fraction 25 that is coloured red/brown, increased adsorption at 300-320 nm was obtained, which was suggested to be characteristic for red/brown coloured polyphenols. The results suggest that XAD 16 treatment can remove the majority of the polyphenols.

Fraction 4 and fraction 9 are lyophilized. The lyophilized product of fraction 4 had a fluffy structure and the color was near-white (absence of chlorophyll). The lyophilized product of fraction 9 was crusty and colorless.

The invention claimed is:

1. A method for isolating a soluble structurally intact plant protein from a plant material on an industrial scale, wherein the method comprises the steps of:
   i) providing the plant material and mechanically disrupting the plant cells of said plant material to obtain a plant juice, wherein before, during, or after the step of disrupting the plant cells an extraction composition comprising a reducing agent and a buffering agent is added to provide for a pH value of about 6-8, ii) treating the plant juice with 10-500 mM of a divalent cation source in combination with a mild heating step to a temperature of between about 40-60° C. that does not change the soluble plant protein, to cause aggregation of chloroplast membranes, iii) separating said aggregated chloroplast membranes from the soluble plant protein in said treated plant juice by precipitation and/or microfiltration to provide a plant juice supernatant or plant juice permeate comprising the soluble plant protein, iv) subjecting the plant juice supernatant or plant juice permeate comprising the soluble plant protein obtained in step iii) to ultrafiltration to provide a soluble plant protein concentrate which is essentially free of salts, phenolic compounds, and the added reducing and buffering agent, and v) subjecting the soluble plant protein concentrate to hydrophobic column adsorption to thereby separate in a single column passage any residual chlorophyll, phenolic compounds and off-odors from the soluble plant proteins to provide a column permeate comprising isolated soluble plant protein that is essentially free of chlorophyll and off-odors, and wherein said method further optionally comprises a steps of:

vi) drying the said column permeate comprising soluble plant protein to provide a powder of functional plant protein, and/or vii) regenerating the hydrophobic adsorption column.

2. The method according to claim 1, wherein the extraction composition further comprises water.

3. The method according to claim 1, wherein the reducing agent is metabisulfite.

4. The method according to claim 1, wherein said plant juice after addition of said extraction composition comprising at least one of a reducing agent and a divalent cation source in step i) comprises a dry matter content of up to 10 wt % based on the total weight of the plant juice.

5. The method according to claim 1, wherein said treating step in step ii) involves heating the plant juice to a temperature of between about 40° C. to 55° C.

6. The method according to claim 1, wherein said precipitation involves centrifugation of the divalent cation-aggregated chloroplast membranes to provide a pellet of aggregated chloroplast membranes and a plant juice supernatant comprising the soluble plant protein, or wherein said microfiltration comprises filtering the juice and/or the divalent cation-aggregated chloroplast membranes through a filter having a pore size in the range of 0.1-0.5 μm.

7. The method according to claim 1, wherein hydrophobic column adsorption comprises the use of a column packed with a hydrophobic adsorptive resin.

8. The method according to claim 1, wherein the steps i), iii), iv), and v) are performed under low temperature, wherein said low temperature is a temperature in the range of about 0-15° C.

9. The method according to claim 1, wherein the processing time to complete process steps i)-v) is no more than 1 day.

10. The method according to claim 1, wherein the protein is ribulose 1,5-diphosphate carboxylase oxygenase (Rubisco).

11. The method according to claim 2, wherein in step iii) of separating said aggregated chloroplast membranes from the soluble, plant protein in the treated plant juice comprises separating said aggregated chloroplast membranes from the soluble plant protein in said heated plant juice by precipitation to provide a plant juice supernatant comprising the soluble plant protein.

12. A protein isolate obtained by a method according to claim 1.

13. A food product comprising a protein isolate according to claim 12.

14. The method according to claim 1, wherein in step iv) the soluble plant protein concentrate comprises 25-50 wt % of protein.

15. The method according to claim 1, wherein the step vi) said drying is performed by lyophilisation or spray drying.

16. The method according to claim 1, wherein in step vii) the regenerating is accomplished by the use of ethanol as an eluent of column-adsorbed compounds.

17. The method according to claim 2, wherein said reducing agent, buffering agent and/or divalent cation source is food grade.

18. The method according to claim 2, wherein said divalent cation source is calcium chloride.

19. The method according to claim 5, wherein after the heating the heated juice is cooled by forced cooling, wherein the heated juice is cooled in less than 60 minutes.

20. The method according to claim 6, wherein said filter has a pore size that retains plant cell membranes, chlorophyll, tannin, virus, bacteria and/or aggregates thereof from said juice while allowing passage of soluble proteins.

21. The method according to claim 7, wherein said hydrophobic adsorptive resin is a non-ionic crosslinked polystyrene resin.

22. The method according to claim 7, wherein said hydrophobic adsorptive resin is a macroreticular styrene-divinylbenzene copolymer matrix.

23. The method according to claim 8, wherein said low temperature is a temperature in the range of about 1-10° C.

24. The method according to claim 8, wherein said low temperature is a temperature in the range of about 2-5° C.

25. The method according to claim 8, wherein also step vi) is performed under low temperature, wherein said low temperature is a temperature in the range of about 0-15° C.

26. The method according to claim 9, wherein the processing time from harvest of the plant material to completion of process step v) is no more than 1 day.

27. The method according to claim 9, wherein the processing time from harvest of the plant material to completion of process step vi) is no more than 1 day.

28. The method according to claim 9, wherein the processing time to complete process steps i)-vi) is no more than 1 day.

29. The protein isolate according to claim 12, wherein said protein isolate, following its isolation, comprises low amounts of tannin, wherein the content of tannin is in the range of 0.05-1.0 wt % based on the total weight of the juice.

30. The protein isolate according to claim 12, wherein said protein isolate is for use as a thickening agent, a foaming agent, an emulsifier and a texturizing agent.

31. The method of claim 1, wherein the ultrafiltration step is carried out in diafiltration mode.

32. The method of claim 1, wherein the mild-heat treatment step ii) is between 1 minute and 3 hours.

33. The method of claim 1, wherein the mild-heat treatment step ii) is between 5 minutes and 1 hour.

* * * * *